(12) United States Patent
Luo

(10) Patent No.: US 11,332,767 B2
(45) Date of Patent: May 17, 2022

(54) NUCLEIC ACIDS AND RECOMBINANT HOST CELLS EXPRESSING ACETYLSEROTONIN O-METHYLTRANSFERASE (ASMT) VARIANTS AND THEIR USE IN PRODUCING MELATONIN

(71) Applicant: Danmarks Tekniske Universitet, Kongens Lyngby (DK)

(72) Inventor: Hao Luo, Kongens Lyngby (DK)

(73) Assignee: Danmarks Tekniske Universitet, Kongens Lyngby (DK)

( * ) Notice: Subject to any disclaimer, the term of this patent is extended or adjusted under 35 U.S.C. 154(b) by 0 days.

(21) Appl. No.: 17/109,715

(22) Filed: Dec. 2, 2020

(65) Prior Publication Data

US 2021/0079433 A1    Mar. 18, 2021

Related U.S. Application Data

(62) Division of application No. 16/302,124, filed as application No. PCT/EP2017/062513 on May 24, 2017, now Pat. No. 10,883,127.

(30) Foreign Application Priority Data

May 24, 2016    (EP) ..................................... 16171032

(51) Int. Cl.
*C12P 17/10*    (2006.01)
*C12N 9/10*    (2006.01)

(52) U.S. Cl.
CPC ............ *C12P 17/10* (2013.01); *C12N 9/1007* (2013.01); *C12Y 201/01004* (2013.01)

(58) Field of Classification Search
CPC .............................. C12P 17/10; C12N 9/1007; C12Y 201/01004
See application file for complete search history.

(56) References Cited

U.S. PATENT DOCUMENTS

| 7,807,421 B2 | 10/2010 | Yabuta et al. |
| 2007/0122802 A1 | 5/2007 | Allan |
| 2014/0134689 A1 | 5/2014 | Lee et al. |

FOREIGN PATENT DOCUMENTS

| WO | WO2002006337 | 1/2002 |
| WO | WO2007052166 | 5/2007 |
| WO | WO2013127914 | 9/2013 |
| WO | WO2013127915 | 9/2013 |
| WO | WO2015032911 | 3/2015 |

OTHER PUBLICATIONS

Zhou et al., Cell Mol Life Sci 63(19-20):2260-2290, 2006.*
Kozak, M., Gene 234:187-208, 1999.*
Botros, H. et al, "Crystal structure and functional mapping of human ASMT, the last enzyme of the melatonin synthesis pathway", Journal of Pineal Research, vol. 54, pp. 46-57, (Jul. 2012).
Byeon, Y. et al, "Cloning and functional characterization of the *Arabidopsis* N-acetylserotonin 0-methyltransferase responsible for melatonin synthesis", Journal of Pineal Research, vol. 60, pp. 65-73, (Jan. 2016).
Cheng, K. et al, "Global metabolic network reorganization by adaptive mutations allows fast growth of *Escherichia coli* on glycerol", Nature Communications, vol. 5:3233, pp. 1-9, (2014).
Kang, K. et al, "Molecular cloning of a plant N-acetylserotonin methyltransferase and its expression characteristics in rice", Journal of Pineal Research, vol. 50, pp. 304-309, (Apr. 2011).
Gibson, R. et al, "Biosynthesis and metabolism of indol-3yl-acetic acid: III. partial purification and properties of a tryptamine-forming I-tryptophan decarboxylase from tomato shoots", Journal of Experimental Botany, vol. 23:76, pp. 775-786, (Aug. 1972).
Lee, S. et al, "Overexpression of ethionine resistance gene for maximized production of S-adenosylmethionine in *Saccharomyces cerevisiae* sake kyokai No. 6", Korean J. Chem. Eng., vol. 27:2, pp. 587-589, (2010).
Moran, G. et al, "Expression and characterization of the catalytic core of tryptophan hydroxylase", The Journal of Biological Chemistry, vol. 273:20: pp. 12259-12266, (1998).
Park, M. et al, "Conversion of 5-hydroxytryptophan into serotonine, by tryptophan decarboxylase in plants, *Escherichia coli*, and yeast", Bioscience, Biotechnology, and Biochemistry, vol. 72:9, pp. 2456-2458, (2008).
Park, S. et al, "Production of serotonin by dual expression of tryptophan decarboxylase and tryptamine 5-hydroxylase in *Escherichia coli*", Appl. Microbiol. Biotechnol., vol. 89, pp. 1387-1394, (2011).
Thomas, K. et al, "Arylalkylamine (serotonin) N-acetyltransferase assay using high-performance liquid chromatography with fluorescence or electrochemical detection of N-acetyltryptamine", Analytical Biochemistry, vol. 184, pp. 228-234, (1990).
Winge, I. et al, "Activation and stabilization of human tryptophan hydroxylase 2 by phosphorylation and 14-3-3 binding", Biochem J., vol. 410, pp. 195-204, (2008).
Liu, Y. et al, "SubName: Full=Uncharacterized protein {ECO:0000313IEnsembl: ENSPAN P00000004828};", XP002760566, Database UniProt [online] Nov. 26, 2014 (Nov. 26, 2014), retrieved from EBI accession No. UNIPROT: AOA096MY35 Database accession No. AOA096MY35.
Zhang, G. et al., "SubName: Full=Acetylserotonin O-methyltransferase {ECO:0000313IEMBL:KFQ94517.1};", DATABASE UniProt [online] Nov. 26, 2014 (Nov. 26, 2014), XP002760567, retrieved from EBI accession No. UNIPROT:AOA091 UVP6 Database accession No. AOA091 UVP6.
Zhang, G. et al, "*Nipponia nippon* (crested ibis) Acetylserotonin O-methyltransferase", XP002760568, Database ENA [online] Jun. 18, 2014 (Jun. 18, 2014), retrieved from EBI accession No. EMBL:KFQ94517 Database accession No. KFQ94517.

(Continued)

*Primary Examiner* — Delia M Ramirez
(74) *Attorney, Agent, or Firm* — McHale & Slavin, P.A.

(57) ABSTRACT

Described herein are variants of acetylserotonin O-methyltransferase (ASMT) as well as vectors and recombinant microbial host cells expressing such ASMT variant and their use in producing melatonin and related compounds. Preferred ASMT variants provide for a higher turnover of N-acetylserotonin into melatonin.

19 Claims, 2 Drawing Sheets

Figure 1:
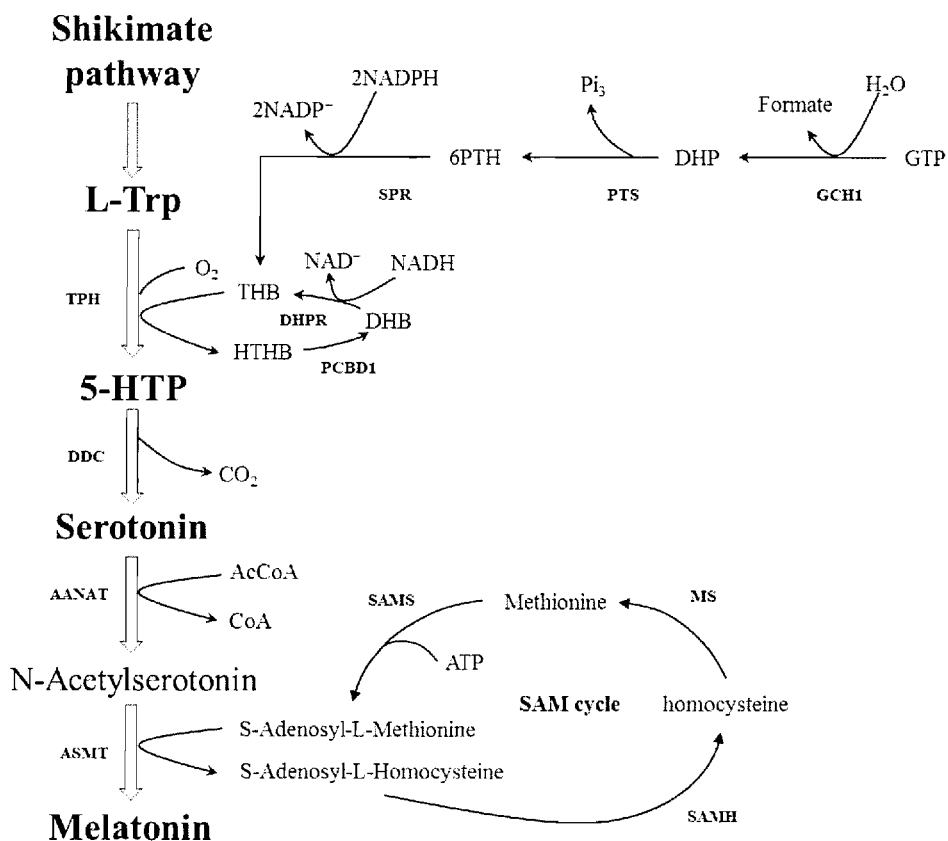

Specification includes a Sequence Listing.

(56) References Cited

OTHER PUBLICATIONS

Coon, S. et al, "acetylserotonin )-methyltransferase [Macaca mulatta]", GenBank accession No. NP_001028112.1, (Apr. 2013).
Pollen, xxx et al, GenBank accession No. PNJ02489, 2018.
Witkowski, A. et al, "Conversion of Beta-ketoacyl synthase to a malonyl decarboxylase by replacement of the active-site cysteine with glutamine", Biochemistry, vol. 38, pp. 11643-11650, (1999).
Tang, S. et al., "Identification of dehalobacter reductive dehalogenases that catalyse dechlorination of chloroform, 1,1,1-trichloroethane and 1,1-dichloroethane", Phil. Trans. of the Royal Soc. B ,vol. 368:Mar. 18, 2012, pp. 1-10, (2013).
Seffernick, J. et al, "Melamine deaminase and atrazine chlorohydrolase: 98 percent identical but functionally different", J. Bacteriol., vol. 183:8, pp. 2405-2410, (2001).
Branden, C. et al, Introduction to protein structure, Garland Publishing, Inc., New York, p. 247, (1991).
Sadowski, M. et al, "The sequence-structure relationship and protein function prediction" Current Opinion in Structural Bbiology, vol. 19, pp. 357-362, (2009).
Zhang, G. et al, "SubName: Full=Acetylserotonin O-methyltransferase {ECO:0000313IEMBL:KF079913.1};", Database UniProt [online] Nov. 26, 2014 (Nov. 26, 2014), retrieved from EBI accession No. UNIPROT:AOA091 GD70 Database accession No. AOA091 GD70.
Corominas, R. et al, "SubName: Full=Acetylserotonin O-methyltransferase isoform A {ECO:0000313IEMBL:AHW56684.1};", Database UniProt [online] Jun. 11, 2014 (Jun. 11, 2014), retrieved from EBI accession No. UNIPROT:X5D311 Database accession No. X5D311.
UniProtKB—P46597, (ASMT_HUMAN), accessed on Apr. 2016, 16 pages.
International Search Report and Written Opinion issued in application PCT/EP2017/062513, completion date Jun. 23, 2017, dated Jul. 18, 2017, 3 pages, European Patent Office.

* cited by examiner

FIG. 3

```
hsASMT        1  MGSS-----------EDQAYRLLNDYANGFMVSQVLFAACELGVFDLLAEAPGPLDVAAV
atASMT        1  MGSTAETQLTPVQVTDDEAALFAMQLASASVLPMALKSALELDLLEIMAKNGSPMSPTEI
btASMT        1  MCSQ-----------EGEGYSLLKEYANGFMVSQVLFAACELGVFELLAEALEPLDSAAV
trASMT        1  M-------------------FLIAHLPLPQVVFSSCELGVFDLLLGAERPLSAEEI
mamuASMT      1  MGSS-----------GDDGYRLLNEYTNGFMVSQVLFAACELGVFDLLAEAPGPLDVAAV
eeASMT        1  MEGP-----------GDRAFRLLNEYSSGFMVSQVLFAACELGVFDLLAQAPEPLDTAEL
consensus     1  *...              .............**..........*.....

hsASMT       50  AAGVRASAHGTELLLDICVSLKLLKVETRGGKAFYRNTELS-------------SDYLTT
atASMT       61  ASKLPTKNPEAPVMLDRIL--RLL----TSYSVLTCSNRKLSGDGVERIYGLGPVCKYLTK
btASMT       50  SSHLGSSPQGTELLLNTCVSLKLLQADVRGGKAVYANTELA-------------STYLVR
trASMT       38  SRALGTSVDGTERLLAACSGLQLLNIHQDNGRCLYSNTDQA-------------SVYLTR
mamuASMT     50  AAGVEASSHGTELLLDTCVSLKLLKVETRAGKAFYQNTELS-------------SAYLTR
eeASMT       50  ATRLGTSLHGTELLLDVCASLELLTVETKRNRAVYQNTDLS-------------TTFLVR
consensus    61  ..  ..   .....*.  .....**  .....    *....         ..*..

hsASMT       97  VSPTSQCS--MLKYMGRTSYRCWGHLADAVREGRNQYLETFGVPAEELFTAIYRSEGERL
atASMT      116  NEDGVSIAALCLMNQDKVLMESWYHLKDAILDGGIPFNKAYGMSAFEYHGTDPRFN---K
btASMT       97  GSPRSQRD--MLLYAGRTAYVCWRHLAEAVREGRNQYLKAFGIPSEELFSAIYRSEDERL
trASMT       85  SSPVSLSQ--SIQYSSRTIYLCWHYLTDAVREGRNQYEKAFGVDAQDLFQALYRSDEEMV
mamuASMT     97  VSPTSQCN--LLKYMGRTSYGCWGHLADAVREGKNQYLQTFGVPAEDLFKAIYRSEGERL
eeASMT       97  TSPTCQLH--MLLYLSRTTYLCWGHLAAAVREGKNQYKRAFGVPSEQLFTAIYRSEAERL
consensus   121  .....     ........*...*....*.... *.......*.......*......

hsASMT      155  QFMQALQEVWSVNGRSVLTAFD-LSVFPLMCDLGGGAGALAKECMSLYPGCKITVFDIPE
atASMT      173  VFNNGMSNHSTITMKKILETYKGFEGLTSLVDVGGGIGATLKMIVSKYPNLKGINFDLPH
btASMT      155  QFMQGLQDVWRLEGATVLAAFD-LSPFPLICDLGGGSGALAKACVSLYPGCRAIVFDIPG
trASMT      143  KFMQLMNSIWNICGKDVVTAFD-LSPFKTICDLGGCSGALAKQCTSAYPECTVTIFDLPK
mamuASMT    155  QFMQALQEVWSVNGRSVLTAFD-LSGFPLMCDLGGGPGALAKECLSLYPGCKVTVFDVPE
eeASMT      155  LFMRGLAEIWSVHGVGVMTAFD-LSAFSVICDLGGASGALARVCASLYPDSSVLVLEVPE
consensus   181  .*........ .......***...*..**...  *.**..*. ..  .*.

▼▼          ▼
hsASMT      214  VVWTAKQHFSFQEEEQIDFQEGDFFKDPLPEADLYILARVLHDWADGKCSHLLERIYHTC
atASMT      233  VIEDAPSHP------GIEHVGLDMFV-SVPKGDAIFMKWICHDWSDEHCVKFLKNCYESL
btASMT      214  VVQIAKRHFSASEDERISFHEGDFFKDALPEADLYILARVLHDWTDAKCSHLLQRVYRAC
trASMT      202  VVRTSRENFFTEANQRIGFCEGDFFKDPLPEADLYVLARILHDWTDQRCLELLRRVHGAC
mamuASMT    214  VVRTAKQHFSFPEEEIHLQEGDFFKDPLPEADLYILARILHDWADGKCSHLLERVYHTC
eeASMT      214  VVRAARSLFLSTVEAPVSFREGDFFKDPLPEADLYILARVLHDWTDEKCSELLAKIHHTC
consensus   241  *.....   ...  . ..**.*...*...****.*...***.* ...*...* hsASMT      274  KPGGGILVIESLLDEDRRGPLLTQ-LYSLN--MLVQ-TEGQERTPTHYHMLLSSAGFRDF
atASMT      286  PEDGKVILAECILPETPDSSLSTKQVVHVDCIMLAHNPGGKERTEKEFEALAKASGFKGI
btASMT      274  RTGGGILVIESLLDTDGRGPLTTL-LYSLN--MLVQ-TEGRERTPAEYRALLGPAGFRDV
trASMT      262  RPGGSVLLVEALLYEDGSGPLTAQ-LYSLN--MLVQ-TEGRERSAAQYAALLTAAGFSNV
mamuASMT    274  KPGGGILVIESLLDEDRRGPLLTQ-LYSLN--MLVQ-TEGQERTPTHYHMLLSSAGFRDF
eeASMT      274  KPGGGILVVESVLEEDRRGPLTTQ-LYSLN--MLVQ-TEGRERTPAEYRSLICSAGFQDF
consensus   301  ...*.....*..*.......*...  *.....**.. ..*.**.....*....**.

hsASMT      330  QFK--KTGAIYDAILAR--K
atASMT      346  KVVCDAFGVNLIELLKK--L
btASMT      330  RCR--RTGGTYDAVLAR--K
trASMT      318  QHR--FTGKIYDAVLARKEA
mamuASMT    330  QFK--KTGAIYDAILVR--K
eeASMT      330  QLK--KTGKIYDVILAR--K
consensus   361  ..   ..*.......*..
```

NUCLEIC ACIDS AND RECOMBINANT HOST CELLS EXPRESSING ACETYLSEROTONIN O-METHYLTRANSFERASE (ASMT) VARIANTS AND THEIR USE IN PRODUCING MELATONIN

CROSS-REFERENCE TO RELATED APPLICATIONS

In accordance with 37 C.F.R. 1.76, a claim of priority is included in an Application Data Sheet filed concurrently herewith. Accordingly, the present invention claims priority as a divisional of U.S. patent application Ser. No. 16/302,124, entitled "VARIANTS OF ACETYLSEROTONIN O-METHYLTRANSFERASE AND USES THEREOF", filed Nov. 16, 2018, now U.S. Pat. No. 10,883,127, which is a § 371 national stage entry of International Application No. PCT/EP2017/062513, entitled "VARIANTS OF ACETYL-SEROTONIN O-METHYLTRANSFERASE AND USES THEREOF", filed May 24, 2017, which claims priority to European Patent Application No. 16171032.2, entitled "VARIANTS OF ACETYLSEROTONIN O-METHYL-TRANSFERASE AND USES THEREOF", filed May 24, 2016, the entire contents of which are incorporated herein by reference.

FIELD OF THE INVENTION

The present invention relates to variants of acetylserotonin O-methyltransferase (ASMT) as well as vectors and recombinant host cells expressing such ASMT variant and their use in producing melatonin. More specifically, the present invention relates to ASMT variants providing for a higher turnover of N-acetylserotonin into melatonin.

BACKGROUND OF THE INVENTION

Melatonin is a powerful antioxidant and maintains the body's circadian rhythm. Over-the-counter dietary supplements based on melatonin have been available for many years in the U.S. While commercial melatonin is typically chemically synthesized, melatonin can also be produced in microbial cells engineered to express an appropriate biosynthetic pathway (see, e.g., WO 2013/127915 A1, WO 2015/032911 A1 and US 2014/134689 AA).

In animals, melatonin is biosynthesized from the native metabolite L-tryptophan via the intermediates 5-hydroxy-L-tryptophan (5HTP), serotonin and N-acetylserotonin. The last step is this pathway, the conversion of N-acetylserotonin and S-adenosyl-L-methionine (SAM) to melatonin and S-adenosyl-L-homocysteine (SAH), is catalyzed by ASMT. The SAH can then be recycled back to SAM via the S-adenosyl-L-methionine cycle in microbial cells where the S-adenosyl-L-methionine cycle is native (e.g., in *E. coli*) or recombinantly introduced. Byeon et al. (2016) and Kang et al. (2011) describe *Arabidopsis* and plant ASMTs, respectively.

Botros et al. (2013) explored the crystal structure of human ASMT (hereinafter "*Homo sapiens* ASMT" or "hsASMT"), described as consisting of a C-terminal domain typical of other SAM-dependent O-methyltransferases, and an N-terminal domain which intertwines several helices with another monomer to form the physiologically active dimer. They also analyzed 20 nonsynonymous hsASMT variants for their activity, finding that the majority of these mutations reduced or abolished ASMT activity. For example, the naturally occurring hsASMT variants P243L, Y248H and I269M exhibited a reduced or abolished enzyme activity. In addition, based on both genetics and biochemical data, it was proposed in WO 2007/052166 (Institut Pasteur) that mutations in the ASMT gene cause an absence or a decrease of melatonin and confer an increased risk to neuropsychiatric disorders such as ASD and ADHD.

For the purpose of biosynthetic production of melatonin, however, there is a need for ASMT variants and recombinant cells providing for an improved production of melatonin.

SUMMARY OF THE INVENTION

The present inventor has found that, surprisingly, mutations in certain residues of ASMT can increase the turnover of N-acetylserotonin into melatonin. In particular, mutations located in or near the opening for the SAM-binding site are advantageous, such as mutations in or structurally adjacent to the helix "guarding" the opening. It was also found that a deletion or downregulation of a gene encoding a cyclopropane fatty acyl phospholipid synthase can increase the yield of melatonin.

Accordingly, in one aspect, the invention relates to a variant of a parent ASMT, the variant comprising a mutation in at least one residue located in the segment corresponding to residues A258-T272, P241-Y248, D259-H271 and/or T307-Q310 of hsASMT, the mutation providing for an increased catalytic activity as compared to the parent ASMT. Examples of ASMTs include, but are not limited to, those listed in Table 1. Preferred mutations include those corresponding to A258E, G260D and T272A in hsASMT.

In other aspects, the invention relates to nucleic acid sequences and vectors encoding such variant ASMTs.

The invention also relates to recombinant host cells. In one aspect, the recombinant host cell comprises such variant ASMTs, nucleic acids and/or vectors. In one aspect, the recombinant host cell is derived from an *E. coli* cell and comprising a heterologous biosynthetic pathway for producing melatonin and a deletion or downregulation of the cfa gene.

In other aspects, the invention relates to the use of such recombinant host cells for producing melatonin.

These and other aspects and embodiments are described in more detail below.

LEGEND TO THE FIGURES

FIG. 1: Metabolic pathways for the production of melatonin according to the invention.

Figure 2:
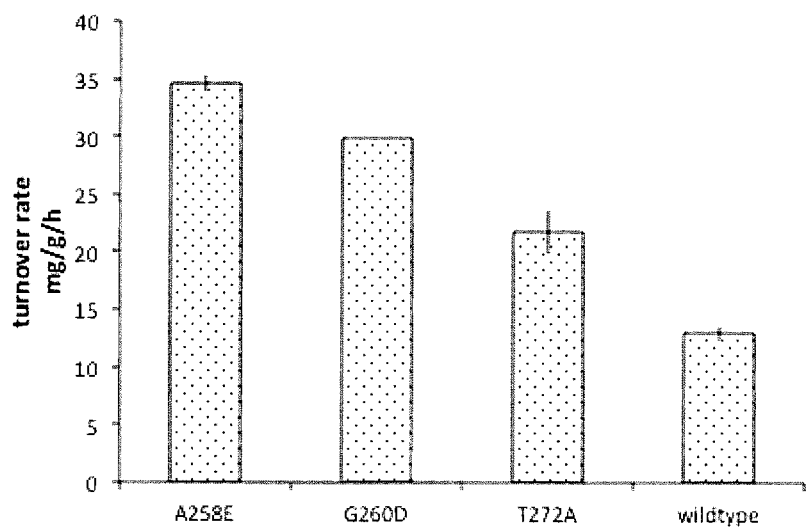

FIG. 2: ASMT turnover rate measurement. Cells expressing various hsASMT variant were grown in M9 medium supplemented with 200 mg/l of acetylserotonin at 37° C. and secretion of melatonin was determined at different time points.

FIG. 3: Protein sequence alignment of 6 functional ASMTs; hsASMT (SEQ ID NO:1), caffeic acid o-methyltransferase from *Ocimum basilicum* (atASMT; SEQ ID NO:2), bovine (*Bos Taurus*) ASMT (btASMT; SEQ ID NO:3), *Takifugu rubripes* ASMT (trASMT; SEQ ID NO:4), *Macaca mulatta* ASMT (mamuASMT; SEQ ID NO:5) and *Elephantulus edwardii* ASMT (eeASMT; SEQ ID NO:6). All of these ASMTs have been functionally tested in *E. coli*.

DETAILED DISCLOSURE OF THE INVENTION

As shown in Example 1 and in FIG. 1, surprisingly, it is possible to improve the catalytic activity of ASMT by engineering specific residues in or near the opening for the SAM-binding site.

In one aspect, the variant ASMT comprises or consists of a mutation in at least one of the residues corresponding to A258, G260 and T272 in *Homo sapiens* ASMT (hsASMT; SEQ ID NO:1). In separate and specific embodiments, the variant ASMT is a variant of hsASMT (SEQ ID NO:1), atASMT (SEQ ID NO:2), btASMT (SEQ ID NO:3), trASMT (SEQ ID NO:4), mamuASMT (SEQ ID NO:5) or eeASMT (SEQ ID NO:6), such as, e.g., hsASMT (SEQ ID NO:1).

In one aspect, the variant ASMT is a variant of *Homo sapiens* ASMT (SEQ ID NO:1), comprising at least one mutation in the segment corresponding to residues A258 to T272, the mutation providing for an increased catalytic activity in converting N-acetylserotonin to melatonin. In one embodiment, the variant comprises a mutation in a residue selected from the group consisting of A258, G260, and T272.

In one aspect, the variant ASMT is a variant of *Homo sapiens* ASMT, the variant having at least 92% sequence identity to *Homo sapiens* ASMT (SEQ ID NO:1) and comprising one or more mutations in the segment corresponding to residues A258 to T272 in *Homo sapiens* ASMT (SEQ ID NO:1), providing for an increased catalytic activity in converting N-acetylserotonin to melatonin as compared to hsASMT. The variant ASMT, may, for example, have at least 93%, at least 94%, at least 95%, at least 96%, at least 97%, at least 98% or at least 99% sequence identity to *Homo sapiens* ASMT (SEQ ID NO:1). In one embodiment, the variant comprises a mutation in a residue selected from the group consisting of A258, G260, and T272.

In specific embodiments, the variant ASMT may have at least about 50%, such as at least about 100%, such as at least about 150%, such as at least about 200% increased catalytic activity in converting N-acetylserotonin to melatonin as compared to hsASMT.

In some embodiments, the mutation in the variant ASMT is an amino acid substitution selected from the group consisting of (a) A258E; (b) G260D, G260N, G260L, and G260I; and (c) T272A and T272G. In a specific embodiment, the mutation is A258E.

In one aspect, there is provided a variant ASMT comprising a sequence selected from SEQ ID NO:1-6, or a catalytically active fragment of any thereof, having a A258E, G260D, G260N, G260L, G260I, T272A or T272G mutation, such as a A258E, G260D or T272A mutation.

In one aspect, there is provided a variant ASMT comprising SEQ ID NO:1, or a catalytically active fragment thereof, having a A258E, G260D, G260N, G260L, G260I, T272A or T272G mutation, such as a A258E, G260D or T272A mutation.

In another aspect, there is provided a nucleic acid sequence encoding the variant ASMT of any one of the aspects or embodiments described herein. The nucleic acid sequence may be comprised in a vector, and optionally operably linked to one or more expression control sequences.

In another aspect, there is provided a recombinant host cell comprising any such variant ASMT, nucleic acid sequence or vector. The recombinant host cell can, for example, be derived from a mammalian cell, a bacterial cell, a yeast cell, a filamentous fungal cell or an algal cell. In one embodiment, the recombinant host cell is derived from an *Escherichia* cell. The recombinant host cell may further comprise a native or heterologous biosynthetic pathway for producing N-acetylserotonin and a native or heterologous pathway for recycling S-adenosyl-L-homocysteine (SAH) into S-adenosyl-L-methionine (SAM). Optionally, the recombinant host cell may also comprise a deletion or downregulation of a gene encoding a cyclopropane fatty acyl phospholipid synthase.

In another aspect, there is provided a recombinant host cell derived from an *E. coli* cell, comprising an ASMT, a native or heterologous biosynthetic pathway for producing N-acetylserotonin, a native or heterologous pathway for recycling SAH into SAM, and a deletion or downregulation of the cfa gene.

In another aspect, there is provided a method of producing melatonin, comprising culturing the recombinant host cell of any aspect or embodiment described herein in a medium comprising a carbon source, and, optionally, isolating melatonin.

Definitions

Unless otherwise specified or contradicted by context, "*Homo sapiens* ASMT", "human ASMT" or "hsASMT" herein refers to the sequence provided by NCBI GI #1170276 and Uniprot reference P46597-1 (SEQ ID NO:1). ASMT is also known as hydroxyindole O-methyltransferase (HIOMT).

As used herein, "exogenous" means that the referenced item, such as a molecule, activity or pathway, is added to or introduced into the host cell or microorganism. An exogenous nucleic acid sequence can, for example, be introduced either as chromosomal genetic material by integration into a host chromosome or as non-chromosomal genetic material such as a plasmid. Such an exogenous nucleic acid sequence can encode an enzyme or enzyme activity which is either heterologous to the host cell or organism in question or which is an endogenous enzyme or enzyme activity in the host cell or organism. Likewise, an exogenous molecule such as a substrate or cofactor can be added to or introduced into the host cell or microorganism, e.g., via adding the molecule to the media in or on which the host cell or microorganism resides.

In the present context the term "heterologous" means that the referenced item, such as a molecule, activity or pathway, does not normally appear in the host cell or microorganism species in question. Typically, a heterologous pathway comprises at least one enzyme or other component which is heterologous to the host cell.

As used herein, the terms "native" or "endogenous" mean that the referenced item is normally present in or native to the host cell or microbial species in question.

As used herein, "upregulating" an endogenous gene means increasing the transcription and/or translation of a gene present in the native host cell genome relative to a control, such as e.g. the unmodified host cell. Methods of upregulating genes are known in the art and include, e.g., introducing a non-native promoter increasing transcription, modifying the native promoter, deleting genes encoding repressor protein, introducing multiple copies of the gene of interest, etc. "Downregulating" an endogenous gene as used herein means to reduce, optionally eliminate, the transcription or translation of an endogenous gene relative to a control, such as, e.g., the unmodified host cell. Methods of down-regulating, disrupting and deleting genes are known to those of skill in the art, and include, e.g., site-directed mutagenesis, genomic modifications based on homologous recombination, RNA degradation based on CAS9, etc.

In the present context, "overexpressing" refers to introducing an exogenous nucleic acid sequence encoding an enzyme which is either heterologous or native to the microbial host cell, or is a functionally active fragment or variant thereof, and expressing the exogenous nucleic acid sequence to increase the enzyme activity in the microbial cell as compared to the microbial host cell without the introduced exogenous nucleic acid sequence, e.g., a native microbial host cell. This can be useful if, e.g., a microbial host cell does not normally contain the enzymatic activity referred to, where the native enzymatic activity is insufficient, or the native enzyme is subjected to unwanted regulation. In such cases, an exogenous nucleic acid sequence encoding an enzyme which is heterologous to the microbial host cell and which has the desired activity and regulation patterns can be introduced. Overexpression of a nucleic acid sequence can be achieved by placing the nucleic acid sequence under the control of a strong promoter. Non-limiting examples of strong promoters suitable for, e.g., *E. coli* cells are Ptrc, Plac, PlacUV5, PT7, and PTrp. Non-limiting examples of strong promoters suitable for, e.g., yeast cells are TEF1, PGK1, HXT7 and TDH3.

As used herein, a gene that is a "homolog" or "homologous" to another gene is generally an ortholog (i.e., a descended from the same ancestral sequence but separated when a species diverges into two separate species) or a paralog (i.e., separated by gene duplication within a genome). Typically, homologous genes encode proteins with a moderate to high sequence identity (e.g., at least about 30%, such as at least about 50%, such as at least about 60%, such as at least about 70%, such as at least about 80%, such as at least about 90%, such as at least about 95%, such as at least about 99%, over at least the catalytically active portion, optionally over the full length) and/or can at least partially substitute for the other protein in terms of function, when transferred from one species into another. Homologs of a particular gene can be identified using publicly available and specialized biological databases, e.g., by the eggNOG, InParanoid, OrthoDB, OrthoMCL, OMA, Roundup, TreeFam, LOFT, Ortholuge, EnsemblCompara GeneTrees and HomoloGene.

A "variant" of a parent or reference enzyme comprises one or more mutations, such as amino acid substitutions, insertions and deletions, as compared to the parent or reference enzyme. Typically, the variant has a high sequence identity to the amino acid sequence of the parent or reference enzyme (e.g., at least about 70%, such as at least about 80%, such as at least about 90%, such as at least about 91%, such as at least about 92%, such as at least about 93%, such as at least abut 94%, such as at least about 95%, such as at least about 96%, such as at least about 97%, such as at least about 98%, such as at least about 99%, over at least the catalytically active portion, optionally over the full length, although less than 100% sequence identity).

Unless otherwise stated, the term "sequence identity" for amino acid sequences as used herein refers to the sequence identity calculated as $(n_{ref}-n_{dif})\cdot 100/n_{ref}$ wherein $n_{dif}$ is the total number of non-identical residues in the two sequences when aligned and wherein $n_{ref}$ is the number of residues in one of the sequences. Hence, the amino acid sequence GSTDYTQNWA will have a sequence identity of 80% with the sequence GSTGYTQAWA ($n_{dif}=2$ and $n_{ref}=10$). The sequence identity can be determined by conventional methods, e.g., Smith and Waterman, (1981), Adv. Appl. Math. 2:482, by the 'search for similarity' method of Pearson & Lipman, (1988), Proc. Natl. Acad. Sci. USA 85:2444, using the CLUSTAL W algorithm of Thompson et al., (1994), Nucleic Acids Res 22:467380, by computerized implementations of these algorithms (GAP, BESTFIT, FASTA, and TFASTA in the Wisconsin Genetics Software Package, Genetics Computer Group). The BLAST algorithm (Altschul et al., (1990), Mol. Biol. 215:403-10) for which software may be obtained through the National Center for Biotechnology Information .ncbi.nlm.nih.gov/) may also be used. When using any of the aforementioned algorithms, the default parameters for "Window" length, gap penalty, etc., are used.

A residue in one amino acid sequence which "corresponds to" a specific reference residue in a reference amino acid sequence is the residue which aligns with the reference residue. Residues in ASMTs from various species which align with specific reference residues in human ASMT (hsASMT) can be identified in the alignment in FIG. 2.

A "fragment" of a protein comprises at least the part of the protein which is responsible for its function of interest, e.g., in the case of an enzyme, its catalytic part. Typically, a "fragment" comprises a segment corresponding to at least about 30%, such as at least about 50%, such as at least about 60%, such as at least about 70%, such as at least about 80%, such as at least about 90%, such as at least about 95%, of the full length protein.

A "functionally active variant" or "functionally active fragment" comprises mutations and/or deletions, respectively, which do not substantially affect the function of the variant or fragment as compared to the parent or reference protein, and can substitute at least partially for the parent or reference protein in terms of the function of interest. Typically, in the case of an enzyme, a functionally active variant or fragment can be described as a catalytically active variant or fragment, and has a catalytic activity, as determined by a suitable activity assay, which is 80-120%, such as 90%-110%, such as 95%-105%, of that of the parent or reference enzyme (which may in itself be a variant of a native enzyme).

As used herein, "vector" refers to any genetic element capable of serving as a vehicle of genetic transfer, expression, or replication for an exogenous nucleic acid sequence in a host cell. For example, a vector may be an artificial chromosome or a plasmid, and may be capable of stable integration into a host cell genome, or it may exist as an independent genetic element (e.g., episome, plasmid). A vector may exist as a single nucleic acid sequence or as two or more separate nucleic acid sequences. Vectors may be single copy vectors or multicopy vectors when present in a host cell. Preferred vectors for use in the present invention are expression vector molecules in which one or more functional genes can be inserted into the vector molecule, in proper orientation and proximity to expression control elements resident in the expression vector molecule so as to direct expression of one or more proteins when the vector molecule resides in an appropriate host cell.

Standard recombinant DNA and molecular cloning techniques useful for construction of appropriate expression vectors and other recombinant or genetic modification techniques for practising the invention, are well known in the art and are described by, e.g., Green and Sambrook, Molecular Cloning, A Laboratory Manual, Cold Spring Harbor Laboratory Press (Cold Spring Harbor, N.Y.) (2012); by Silhavy, T. J., Bennan, M. L. and Enquist, L. W. Experiments with Gene Fusions; Cold Spring Harbor Laboratory: Cold Spring Harbor, N.Y. , 1984; by Ausubel et al., Short Protocols in Molecular Biology, Current Protocols, John Wiley and Sons (New Jersey) (2002), and references cited herein. Appropriate microbial cells and vectors are available commercially through, for example, the American Type Culture Collection (ATCC), Rockville, Md.

The term "host cell" refers to any cell into which an exogenous nucleic acid sequence can be introduced and expressed, typically via an expression vector. The host cell may, for example, be a wild-type cell isolated from its natural environment, a mutant cell identified by screening, a cell of a commercially available strain, or a genetically engineered cell or mutant cell, comprising one or more other exogenous and/or heterologous nucleic acid sequences than those of the invention.

A "recombinant" cell or host cell as used herein refers to a host cell into which one or more exogenous nucleic acid sequences of the invention have been introduced, typically via transformation of a host cell with a vector.

The term "substrate" or "precursor", as used herein in relation to a specific enzyme, refers to a molecule upon which the enzyme acts to form a product. When used in relation to an exogenous biometabolic pathway, the term "substrate" or "precursor" refers to the molecule(s) upon which the first enzyme of the referenced pathway acts. When referring to an enzyme-catalyzed reaction in a microbial cell, an "endogenous" substrate or precursor is a molecule which is native to or biosynthesized by the microbial cell, whereas an "exogenous" substrate or precursor is a molecule which is added to the microbial cell, via a medium or the like.

Enzymes referred to herein can be classified on the basis of the handbook Enzyme Nomenclature from NC-IUBMB, 1992), see also the ENZYME site at the internet: .expasy.ch/enzyme/. This is a repository of information relative to the nomenclature of enzymes, and is primarily based on the recommendations of the Nomenclature Committee of the International Union of Biochemistry and Molecular Biology (IUB-MB). It describes each type of characterized enzyme for which an EC (Enzyme Commission) number has been provided (Bairoch A., The ENZYME database, 2000, Nucleic Acids Res 28:304-305). The IUBMB Enzyme nomenclature is based on the substrate specificity and occasionally on their molecular mechanism.

Specific Embodiments of the Invention

Preferred ASMT variants are described below, together with other enzymes in preferred biosynthetic pathways for production of melatonin in recombinant microbial cells (see, e.g., FIG. 1).

Acetylserotonin O-Methyltransferase (ASMT)

ASMT is typically classified as EC 2.1.1.4. Sources of nucleic acid sequences encoding a native ASMT into which the mutations described herein can be introduced include any species where the encoded gene product is capable of catalyzing the referenced reaction, including humans and other mammalian and non-mammalian animals, plants, etc. ASMTs particularly suitable for *E. coli* and other microbial host cells include those whose amino acid sequence are shown in FIG. 3, i.e., *Homo sapiens, Ocimum basilicum, Bos Taurus, Takifugu rubripes, Macaca mulatta* and *Elephantulus edwardii* ASMT. Particularly preferred is hsASMT.

Examples of nucleic acids encoding ASMT for use in aspects and embodiments of the present invention include, but are not limited to, those encoding the ASMTs listed in Table 1, as well as functionally active variants, homologs and fragments thereof. In one embodiment, the ASMT is hsASMT or a functionally (catalytically) active fragment or variant thereof.

Functional fragments and variants of ASMT enzymes are known in the art. For example, to increase heterologous expression in *E. coli* and/or the enzyme stability, the ASMT sequence can be truncated to remove portions not needed for its catalytic activity while preserving the catalytic core of the enzyme, e.g., by 1, 2, 3, 4, 5, 10, 20 or more amino acid residues from the C, terminal, N-terminal, or both. Other ASMT sequences can be similarly truncated to create functionally active fragments or variants comprising the catalytic core.

Many naturally occurring variants of human ASMT are known, though primarily variants in which the mutation has either no significant effect on catalytic activity or reduces or abolishes the catalytic activity. For example, in the UniProt entry for hsASMT (P46597; accessed on Apr. 13, 2016), N13H, K81E and R111K were described as having "no effect on enzyme activity;" E61Q, P243L, I269M, C273S, G278A and V305M are described as "reduced enzyme activity;" and N17K, V171M, D210G, Y248H, R291Q and L298F are described as "nearly abolishes enzyme activity." Accordingly, ASMT variants of the present invention do not comprise N17K, V171M, D210G, Y248H, R291Q and L298F mutations, and do not comprise E61Q, P243L, I269M, C273S, G278A and V305M as the sole mutation. In one embodiment, the ASMT variant does not comprise any of N17K, V171M, D210G, Y248H, R291Q, L298F, E61Q, P243L, I269M, C273S, G278A and V305M As described herein, the ASMT variants provided by the invention comprise a mutation in at least one residue located in a segment corresponding to residues A258-T272 of hsASMT, the mutation providing for an increased catalytic activity. In one embodiment, the ASMT variant comprises only one mutation in the segment in question. Additionally or alternatively, the ASMT variant may comprise one or more mutations in the segments corresponding to P241-Y248, D259-H271 and T307-Q310, the mutation providing for retained or increased ASMT activity. Catalytically active fragments or variants of such ASMT variants are also contemplated, in particular catalytically active fragments or variants in which the increased catalytic activity is not reduced or abolished. In one embodiment, the ASMT comprises only one mutation as compared to the native ASMT amino acid sequence.

In separate and specific embodiments, the ASMT variant comprises a mutation in a residue corresponding to a hsASMT residue listed below, resulting in one of the indicated amino acid substitutions in one, two or all of the indicated amino acid residues:

A258=>E
G260=>D, N, L, or I
T272=>A or G

Particularly contemplated are variants of the ASMTs listed in Table 1 and/or in FIG. 5 of Botros et al. (2013), in particular SEQ ID NOS:1-6 or other ASMTs where at least one residue adjacent to the residue aligning with hsASMT residues A258, G260 or T272 is the same as the adjacent residue in hsASMT. Preferred mutations include those corresponding to A258E, G260D and T272A in hsASMT. In one embodiment, the ASMT variant, or a catalytically active fragment or variant thereof, comprises an A258E mutation. In one embodiment, the ASMT variant, or a catalytically active fragment or variant thereof, comprises a G260D mutation. In one embodiment, the ASMT variant, or a catalytically active fragment or variant thereof, comprises a T272A mutation.

Preferred variants are those that have a sequence identity of at least about 80%, such as least about 90%, such as at least about 91%, such as at least about 92%, such as at least about 93%, such as at abut 94%, such as at least about 95%, such as at least about 96%, such as at least 97%, such as at least about 98%, such as at least about 99%, over at least the catalytically active portion of hsASMT, optionally over the full length of hsASMT (although less than 100% sequence identity to hsASMT).

Nucleic acid sequences and vectors encoding the variant ASMTs, or functionally (catalytically) active fragments or variants thereof, as well as recombinant host cells expressing variant ASMTs from such nucleic acid sequences or vectors, are also contemplated. In a preferred embodiment, the nucleic acid sequence encoding the ASMT is operably linked to a strong promoter such as the Trc promoter, providing for high expression levels of the ASMT in an *E. coli* host.

Suitable assays for testing melatonin production by an ASMT in vitro or in a recombinant microbial host cell include the assay used in Example 1 under the heading "hsASMT variants characterization" as well as the assay described in Kang et al. J. Pineal Res. 2011: 50;304-309, which is hereby incorporated by reference in its entirety. For example, to identify a mutation providing for an increased catalytic activity, the following methods can be used:

Introduce the desired genetic change into a gene encoding an ASMT, e.g., from *Homo sapiens*, using standard molecular biology techniques (Step 1). Express the ASMT variant in a chosen host cell, e.g., *E. coli* (Step 2). To determine ASMT activity in the in vivo host cell system, cultivate the ASMT expressing host cells in the presence of acetylserotonin at a defined concentration, sampling the cell broth periodically during active growth (Step 3a), then determine the levels of accumulated melatonin by known analytical techniques and estimate the turnover rate (Step 4a). To determine ASMT activity in vitro, harvest variant ASMT protein from the host cells by means of protein purification (Step 3b), and determine the enzyme kinetics (Step 4b).

Using such assays, or some other assay known in the art for determining ASMT catalytic activity in converting N-acetylserotonin to melatonin, an increased catalytic activity can be identified for ASMT variants providing for a higher turnover rate or a higher total yield in the referenced reaction as compared to a control value, e.g., the turnover rate or total yield of the native ASMT in the same assay. Preferably, using the ASMT variant, the turnover rate or total yield is at least 5% higher, at least 10% higher, at least 25% higher, at least 50% higher (i.e., at least 1.5-fold), at least 100% higher (i.e., at least 2-fold), at least 150% higher (i.e., at least 2.5-fold) or at least 200% higher (i.e., at least 3-fold) than the control, e.g., the turnover rate or total yield when using the native ASMT.

L-Tryptophan Hydroxylase (TPH)

Sources of nucleic acid sequences encoding a TPH include any species where the encoded gene product is capable of catalyzing the referenced reaction, including humans, mammals such as, e.g., mouse, cow, horse, chicken and pig, as well as other animals such as, e.g., the parasite *Schistosoma mansoni*. In humans and, it is believed, in other mammals, there are two distinct TPH alleles, referred to herein as TPH1 and TPH2, respectively. As shown in FIG. 1, TPHs typically require a cofactor; tetrahydrobiopterin (THB, alternatively abbreviated as BH4). It has been reported, however, that native tetrahydromonapterin (MH4) can replace or substitute for THB as a TPH cofactor (US 2014/0134689 AA).

Examples of nucleic acids encoding L-tryptophan hydroxylase for use in aspects and embodiments of the present invention include, but are not limited to, those encoding the TPHs listed in Table 1, as well as functionally active variants, homologs and fragments thereof.

Functional fragments and variants of TPH enzymes are known in the art. For example, to increase heterologous expression in *E. coli* and the enzyme stability, the TPH sequence can be truncated to remove portions not needed for its catalytic activity which preserving the catalytic core of the enzyme. Specific examples of functional fragments of TPH include Met102 to Ser416 of *Oryctolagus cuniculus* TPH (Moran et al., J Biol Chem 1998; 273(20): 12259-66) and residues Asp45-Arg471 or Glu147-Thr460 (i.e., E147 to T460) of *Homo sapiens* TPH2, optionally adding an N-terminal methionine residue Other TPH sequences can be similarly truncated to create functionally active fragments or variants comprising the catalytic core. For example, the TPH identified as "*Homo sapiens* TPH2, truncated ((45-471)+20)" in Table 1 represents a fragment of *Homo sapiens* TPH2 comprising an added heterologous 20-amino acid polypeptide at its C-terminal, and the *Homo sapiens* TPH2 sequence denoted "*Homo sapiens* TPH2, insert (+6)" has a 6-amino acid insert in the N-terminal portion. Any one of these mammalian TPHs, such as *Homo sapiens* TPH2, or a fragment and/or variant thereof, can be used for catalyzing the hydroxylation of tryptophan, e.g., in a recombinant microbial cell. Notably, *Schistosoma mansoni* TPH (see Table 1) has advantageous properties with respect to, e.g., solubility, thus enabling no or less truncation of the enzyme sequence. Accordingly, *Schistosoma mansoni* TPH, or a functionally active fragment and/or variant thereof, can also be used.

Assays for measuring L-tryptophan hydroxylase activity in vitro are well-known in the art (see, e.g., Winge et al., Biochem J, 2008; 410:195-204 and Moran et al., 1998).

In the recombinant host cell, the L-tryptophan hydroxylase is typically sufficiently expressed so that an increased level of 5HTP production from L-tryptophan can be detected as compared to the microbial host cell prior to transformation with the TPH, optionally in the presence of added THB cofactor and/or tryptophan substrate. Alternatively, the expression level of the specific TPH enzyme can be evaluated by proteomic analysis, according to methods known in the art. In a preferred embodiment, the nucleic acid sequence encoding the TPH is operably linked to a strong promoter such as the Trc promoter, providing for high expression levels of the TPH.

5HTP Decarboxylase

The last step in the serotonin biosynthesis via a 5HTP intermediate, the conversion of 5HTP to serotonin, is in animal cells catalyzed by a 5HTP decarboxylase, which is an aromatic L-amino acid decarboxylase (AADC) typically classified as EC 4.1.1.28. Suitable 5HTP decarboxylases include any tryptophan decarboxylase (TDC) capable of catalyzing the referenced reaction. TDC participates in the plant serotonin biosynthesis pathway, where tryptophan decarboxylase (TDC) catalyzes the conversion of tryptophan to tryptamine, which is then converted into serotonin in a reaction catalyzed by tryptamine 5-hydroxylase (T5H). TDC likewise belongs to the aromatic amino acid decarboxylases categorized in EC 4.1.1.28, and can be able to convert 5HTP to serotonin and carbon dioxide (see, e.g., Park et al., Biosci. Biotechnol. Biocem. 2008; 72(9):2456-2458.2008, and Gibson et al., J. Exp. Bot. 1972; 23(3):775-786), and thus function as a 5HTP decarboxylase. Exemplary nucleic acids encoding ADDC enzymes for use in aspects and embodiments of the present invention include, but are not limited to, those encoding the 5HTP decarboxylases listed in Table 1, as well as functionally active variants, homologs and fragments thereof. In some embodiments, particularly where it is desired to also promote serotonin formation from a tryptamine substrate in the same recombinant cell, an enzyme capable of catalyzing both the conversion of tryptophan to tryptamine and the conversion of 5HTP to serotonin can be used. For example, rice TDC and tomato TDC can function also as a 5HTP decarboxylase, an activity which can be promoted by the presence of pyridoxal phosphate (e.g., at a concentration of about 0.1 mM) (Park et al., 2008). Preferred, non-limiting sources of 5HTP decarboxylase include *Candidatus Koribacter versatilis* Ellin345, *Draconibacterium orientale* and *Verrucosispora maris* (Table 1).

Suitable assays for testing serotonin production by a 5HTP decarboxylase in a recombinant microbial host cell are provided in, or can be adapted from, e.g., Park et al. (2008) and Park et al., Appl Microbiol Biotechnol 2011; 89(5):1387-1394. For example, these assays can be adapted to test serotonin production by a 5HTP decarboxylase (e.g., a TDC), either from 5HTP or, in case the microbial cell comprises an L-tryptophan hydroxylase, from L-tryptophan (or simply a carbon source). In one exemplary embodiment, the recombinant microbial cell produces at least 5%, such as at least 10%, such as at least 20%, such as at least 50%, such as at least 100% or more serotonin than the recombinant cell without transformation with 5HTP decarboxylase enzyme, i.e., a background value.

Serotonin Acetyltransferase (AANAT)

In one aspect, the recombinant microbial cell further comprises an exogenous nucleic acid sequence encoding a serotonin acetyltransferase, also known as serotonin —N-acetyltransferase, arylalkylamine N-acetyltransferase and AANAT, and typically classified as EC 2.3.1.87. AANAT catalyzes the conversion of acetyl-CoA and serotonin to CoA and N-acetylserotonin (FIG. 1). Exemplary nucleic acids encoding AANAT enzymes for use in aspects and embodiments of the present invention include, but are not limited to, those encoding the AANATs shown in Table 1, as well as functionally active variants, homologs or fragments thereof. Suitable assays for testing N-acetylserotonin production by an AANAT in a recombinant microbial host cell are described in, e.g., Thomas et al., Analytical Biochemistry 1990; 184:228-34.

TABLE 1

Examples of enzymes and amino acid sequences

| Name (EC #) | Species | NCBI or UniProtKB[1] accession No. (SEQ ID) |
|---|---|---|
| acetylserotonin O-methyltransferase (EC 2.1.1.4) (ASMT) | *Homo sapiens* | P46597-1, v1 (1) |
| | *Ocimum basilicum* | Q9XGV9-1, v1 (2) |
| | *Bos taurus* | P10950-1, v2 (3) |
| | *Takifugu rubripes* | XP_011609423.1 (4) |
| | *Macaca mulatta* | NP_001028112.1 (5) |
| | *Elephantulus edwardii* | XP_006902482.1 (6) |
| | *Oryza sativa* | XP_015610997.1 (7) |
| | *Rattus norvegicus* | NP_653360.2 (8) |
| | *Gallus gallus* | NP_990674.1 (9) |
| | *Chromobacterium violaceum* | WP_011135808.1 (10) |
| | *Desulfotomaculum kuznetsovii* DSM 6115 | YP_004515712.1 (11) |
| | *Xenopus (Silurana) tropicalis* | NP_001011409.1 (12) |
| | *Pseudomonas fluorescens* | WP_019095725.1 (13) |
| | *Candidatus Solibacter usitatus* | WP_011682595.1 (14) |
| | *Fenneropenaeus chinensis* | AAZ66373.1 (15) |
| | *Arabidopsis thaliana* | NP_200227.1 (16) |
| L-tryptophan hydroxylase (EC 1.14.16.4) (TPH) | *Oryctolagus cuniculus* TPH1 | P17290-1, v2 |
| | *Homo sapiens* TPH1 | NP_004170.1 |
| | *Homo sapiens* TPH2 | NP_775489.2 |
| | *Gallus gallus* | NP_990287.1 |
| | *Mus musculus* | NP_033440.1 |
| | *Equus caballus* | NP_001075252.1 |
| | *Schistosoma mansoni* | AAD01923.1 |
| | *Homo sapiens* TPH2, insert (+6) | (17) |
| | *Homo sapiens* TPH2, truncated ((45-471)+20) | (18) |
| | *Homo sapiens* TPH2, truncated (45-471) | (19) |
| | *Homo sapiens* TPH2, truncated (146-460) | (20) |
| 5HTP decarboxylase (EC 4.1.1.28) (ADDC) | *Acidobacterium capsulatum* | WP_015898075.1 |
| | *Rattus norvegicus* | XP_006251536.1 |
| | *Sus scrofa* | NP_999019.1 |
| | *Homo sapiens* | P20711-1, v2 |
| | *Capsicum annuum* | NP_001312016.1 |
| | *Drosophila caribiana* | AAM80956.1 |
| | *Maricaulis maris* (strain MCS10) | ABI65701.1 |
| | *Oryza sativa* subsp. *Japonica* | XP_015648768.1 |
| | *Pseudomonas putida* S16 | WP_013972057.1 |
| | *Catharanthus roseus* | P17770-1, v1 |
| serotonin acetyltransferase (EC 2.3.1.87 or 2.3.1.5) (AANAT) | *Chlamydomonas reinhardtii* | BAH10512.1 |
| | *Bos Taurus*, optionally with A55P mutation | DAA18183.1 |
| | *Gallus gallus* | NP_990489.1 |
| | *Homo sapiens* | NP_001079.1 |
| | *Mus musculus* | XP_011246971.1 |
| | *Oryctolagus cuniculus* | XP_008249128.1 |
| | *Ovis aries* | NP_001009461.1 |

Variants or homologs of any one or more of the enzymes and other proteins listed in Table 1, having the referenced activity and a sequence identity of at least 30%, such as at least 50%, such as at least 60%, such as at least 70%, such as at least 80%, such as at least 90%, such as at least 95%, such as at least 99%, over at least the catalytically active portion, optionally over the full length, of the reference amino acid sequence, are also contemplated. The variant or homolog may comprise, for example, 2, 3, 4, 5 or more, such as 10 or more, amino acid substitutions, insertions or deletions as compared to the reference amino acid sequence. In particular conservative substitutions are considered. These are typically within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter specific activity are known in the art and are described, for example, by H. Neurath and R. L. Hill, 1979, In: The Proteins, Academic Press, New York. The most commonly occurring exchanges are Ala to Ser, Val to Ile, Asp to Glu, Thr to Ser, Ala to Gly, Ala to Thr, Ser to Asn, Ala to Val, Ser to Gly, Tyr to Phe, Ala to Pro, Lys to Arg, Asp to Asn, Leu to Ile, Leu to Val, Ala to Glu, and Asp to Gly. Homologs, such as orthologs or paralogs, having the desired activity can be identified in the same or a related animal or microbial species using the reference sequences provided and appropriate activity testing. Specific enzyme variants are exemplified herein.

A nucleic acid sequence encoding an enzyme or other protein activity listed in Table 1 may encode an amino acid sequence that is homologous (i.e., native) or heterologous to the recombinant host cell in question.

Vectors

Also provided are vectors comprising nucleic acid sequences according to the above aspects and embodiments, e.g., encoding an ASMT variant and, optionally, one or more of a TPH, a 5HTP decarboxylase and an AANAT and/or enzymes for biosynthesizing or regenerating co-factors needed for ASMT and TPH.

The specific design of the vector depends on, e.g., whether host cell already endogenously produces sufficient amounts of one or more of the enzymes or cofactors. For example, in an E. coli host cell, it may not be necessary to introduce the nucleic acid sequence encoding a GCH1 (FolE) sequence exogenously, in case sufficient amounts of the enzyme is expressed from the native gene or in case the endogenous gene is upregulated. Additionally, for transformation of a particular host cell, two or more vectors with different combinations of the enzymes used in the present invention can be applied. Accordingly, the nucleic acid sequences encoding the ASMT variant and the one or more additional enzymes may be located on the same vector, or on two or more different vectors. The vector can be a plasmid, phage vector, viral vector, episome, an artificial chromosome or other polynucleotide construct, and may, for example, include one or more selectable marker genes and appropriate expression control sequences.

Generally, regulatory control sequences are operably linked to the encoding nucleic acid sequences, and include constitutive, regulatory and inducible promoters, transcription enhancers, transcription terminators, and the like which are well known in the art. The encoding nucleic acid sequences can be operationally linked to one common expression control sequence or linked to different expression control sequences, such as one inducible promoter and one constitutive promoter.

The procedures used to ligate the various regulatory control and marker elements with the encoding nucleic acid sequences to construct the vectors of the present invention are well known to one skilled in the art (see, e.g., Sambrook et al., 2012, supra). In addition, methods have recently been developed for assembling of multiple overlapping DNA molecules (Gibson et al., 2008) (Gibson et al., 2009) (Li & Elledge, 2007), allowing, e.g., for the assembly multiple overlapping DNA fragments by the concerted action of an exonuclease, a DNA polymerase and a DNA ligase.

The promoter sequence is typically one that is recognized by the intended host cell. For an E. coli host cell, suitable promoters include, but are not limited to, the lac promoter, the T7 promoter, pBAD, the tet promoter, the Lac promoter, the Trc promoter, the Trp promoter, the recA promoter, the λ (lamda) promoter, and the PL promoter. Preferred promoters include the Trc promoter. For Streptomyces host cells, suitable promoters include that of Streptomyces coelicolor agarase (dagA). For a Bacillus host cell, suitable promoters include the sacB, amyL, amyM, amyQ, penP, xylA and xylB. Other promoters for bacterial cells include prokaryotic beta-lactamase (Villa-Kamaroff et al., 1978, Proceedings of the National Academy of Sciences USA 75: 3727-3731), and the tac promoter (DeBoer et al., 1983, Proceedings of the National Academy of Sciences USA 80: 21-25). For an S. cerevisiae host cell, useful promoters include the TEF1, HXT7, TDH3, ENO-1, GAL1, ADH1, ADH2, GAP, TPI, CUP1, PHO5 and PGK, such as PGK1 promoters. Other useful promoters for yeast host cells are described by Romanos et al., 1992, Yeast 8: 423-488. Still other useful promoters for various host cells are described in "Useful proteins from recombinant bacteria" in Scientific American, 1980, 242: 74-94; and in Sambrook et al., 2012, supra.

In one embodiment, one or more or all of the exogenous nucleic acids is each under the control of a strong promoter, e.g., each separately selected from Trc, lac, lacUV5, Trp, T7, trac and PL promoter in an E. coli host cell, and each separately selected from PGK1, TEF1, HXT7 and TDH3 in an S. cerevisiae host cell.

A transcription terminator sequence is a sequence recognized by a host cell to terminate transcription, and is typically operably linked to the 3' terminus of an encoding nucleic acid sequence. Suitable terminator sequences for E. coli host cells include the T7 terminator region. Suitable terminator sequences for yeast host cells such as S. cerevisiae include CYC1, PGK, GAL, ADH, AOX1 and GAPDH. Other useful terminators for yeast host cells are described by Romanos et al., 1992, supra.

A leader sequence is a non-translated region of an mRNA which is important for translation by the host cell. The leader sequence is typically operably linked to the 5' terminus of a coding nucleic acid sequence. Suitable leaders for yeast host cells include S. cerevisiae ENO-1, PGK, alpha-factor, ADH2/GAP, TEF, and Kozak sequence.

A polyadenylation sequence is a sequence operably linked to the 3' terminus of a coding nucleic acid sequence which, when transcribed, is recognized by the host cell as a signal to add polyadenosine residues to transcribed mRNA. Useful polyadenylation sequences for yeast host cells are described by Guo and Sherman, 1995, Mol Cell Biol 15: 5983-5990.

A signal peptide sequence encodes an amino acid sequence linked to the amino terminus of an encoded amino acid sequence, and directs the encoded amino acid sequence into the cell's secretory pathway. In some cases, the 5' end of the coding nucleic acid sequence may inherently contain a signal peptide coding region naturally linked in translation reading frame, while a foreign signal peptide coding region may be required in other cases. Useful signal peptides for yeast host cells can be obtained from the genes for *S. cerevisiae* alpha-factor and invertase. Other useful signal peptide coding regions are described by Romanos et al., 1992, supra. An exemplary signal peptide for an *E. coli* host cell can be obtained from alkaline phosphatase. For a *Bacillus* host cell, suitable signal peptide sequences can be obtained from alpha-amylase and subtilisin. Further signal peptides are described by Simonen and Palva, 1993, Microbiological Reviews 57: 109-137.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tec, and tip operator systems. For example, one or more promoter sequences can be under the control of an IPTG inducer, initiating expression of the gene once IPTG is added. In yeast, the ADH2 system or GAL1 system may be used. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the respective encoding nucleic acid sequence would be operably linked with the regulatory sequence.

The choice of the vector will typically depend on the compatibility of the vector with the host cell into which the vector is to be introduced. The vectors may be linear or closed circular plasmids. The vector may also be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. The selectable marker genes can, for example, provide resistance to antibiotics or toxins, complement auxotrophic deficiencies, or supply critical nutrients not in the culture media, and/or provide for control of chromosomal integration. Examples of bacterial selectable markers are the dal genes from *Bacillus subtilis* or *Bacillus licheniformis*, or markers which confer antibiotic resistance such as ampicillin, kanamycin, chloramphenicol, or tetracycline resistance. Suitable markers for yeast host cells are ADE2, HIS3, LEU2, LYS2, MET3, TRP1, and URA3.

The vectors of the present invention may also contain one or more elements that permit integration of the vector into the host cell genome or autonomous replication of the vector in the cell independent of the genome. For integration into the host cell genome, the vector may rely on an encoding nucleic acid sequence or other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity with the corresponding target sequence to enhance the probability of homologous recombination. The integrational elements may be any sequence that is homologous with the target sequence in the genome of the host cell. The integrational elements may, for example, non-encoding or encoding nucleotide sequences. The vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication which functions in a cell. The term "origin of replication" or "plasmid replicator" is defined herein as a nucleotide sequence that enables a plasmid or vector to replicate in vivo. Examples of bacterial origins of replication are the origins of replication of plasmids pBR322, pUC19, pACYC177, and pACYC184 permitting replication in *E. coli*, and pUB1 10, pE194, pTA1060, and pAMβi permitting replication in *Bacillus*. Examples of origins of replication for use in a yeast host cell are the 2 micron origin of replication, ARS1, ARS4, the combination of ARS1 and CEN3, and the combination of ARS4 and CEN6.

More than one copy of the nucleic acid sequence encoding the enzyme or protein of interest may be inserted into the host cell to increase production of the gene product. An increase in the copy number of the encoding nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the sequence, can be selected for by cultivating the cells in the presence of the appropriate selectable agent.

Recombinant Host Cells

Recombinant host cells expressing ASMT variants, optionally from the above-described nucleic acid sequences or vectors, are also provided. Suitable host cells for expressing ASMT variants include, for example, mammalian and microbial cells. Once expressed, the ASMT variants can, optionally, be retrieved and purified from the host cells or the cell medium in which the host cells are grown.

The recombinant host cell can also be capable of producing melatonin. For example, mammalian cells comprising a native biosynthetic pathway for melatonin can be transformed with a vector expressing an ASMT variant according to the present invention, under the control of a promoter suitable for the selected mammalian host cell. Alternatively, the recombinant host cell of the invention can be prepared from any host cell by introducing heterologous or overexpressing endogenous enzymes of the necessary biometabolic pathways, using recombinant techniques well known in the art and cited elsewhere herein.

The host cell is preferably tryptophan autotrophic (i.e., capable of endogenous biosynthesis of L-tryptophan), grows on synthetic medium with suitable carbon sources, and expresses a suitable RNA polymerase (such as, e.g., T7 polymerase). In all known microorganisms, tryptophan production takes place via a single metabolic pathway (Somerville, R. L., Herrmann, R. M., 1983, Amino acids, Biosynthesis and Genetic Regulation, Addison-Wesley Publishing Company, U.S.A.: 301-322 and 351-378; Aida et al., 1986, Bio-technology of amino acid production, progress in industrial microbiology, Vol. 24, Elsevier Science Publishers, Amsterdam: 188-206). Tryptophan can also or alternatively be added to the medium of a recombinant host cell comprising TPH, ASMT and other enzymes providing for a melatonin biosynthetic pathway.

The recombinant host cell is typically capable of biosynthesizing and/or regenerating the cofactors used by the enzymes in the melatonin biosynthesis pathway. In particular, the recombinant host cell is preferably capable of biosynthesizing, regenerating, or bio-synthesizing and regenerating, one or more cofactors for TPH, AANAT and ASMT (FIG. 1).

To provide cofactor for TPH-catalyzed hydroxylation of tryptophan, the recombinant host cell is preferably capable of biosynthesizing one or both of THB and MH4 via endogenous or heterologous (introduced) pathways. For example, endogenous pathways for THB biosynthesis are present in mammalian cells. Microbial cells generally do not biosynthesize THB endogenously, but it has been reported that the endogenous compound MH4 may substitute for or replace THB as cofactor for TPH in such cells (US 2014/134689 AA; University of California). GTP cyclohydrolase I (such as, e.g. FolE)-catalyzed pterin biosynthesis resulting in MH4 takes place in many organisms including both prokaryotes and eukaryotes (see, e.g. FIG. 9 of US 2014/134689 AA). So, for example, in one embodiment, the microbial host cell is an $E.\ coli$ cell comprising the endogenous enzymes folE, folX, P-ase, and folM, optionally upregulated or expressed from one or more endogenous vectors.

Alternatively, enzymes of biosynthetic pathways for producing and/or regenerating THB can be introduced recombinantly, as described in WO 2013/127914 A1, WO 2013/127915 A1 and WO 2015/032911 A1 (Danmarks Tekniske Universitet) and in US 2014/134689 AA (University of California), all of which hereby incorporated by reference in their entireties. Briefly, in one embodiment, the recombinant cell comprises an exogenous pathway producing THB from GTP and herein referred to as "first THB pathway", comprising a GTP cyclohydrolase I (GCH1), a 6-pyruvoyl-tetrahydropterin synthase (PTPS), and a sepiapterin reductase (SPR) (see FIG. 1). The addition of such a pathway to microbial cells such as $E.\ coli$ (JM101 strain), $S.\ cerevisiae$ (KA31 strain) and $Bacillus\ subtilis$ (1A1 strain (TrpC2)) has also been described in, e.g., U.S. Pat. No. 7,807,421. In one embodiment, the recombinant cell comprises a pathway producing THB by regenerating THB from HTHB, herein referred to as "second THB pathway", comprising a 4a-hydroxytetrahydrobiopterin dehydratase (PCBD1) and a 6-pyruvoyl-tetrahydropterin synthase (DHPR). As shown in FIG. 1, the second THB pathway converts the HTHB formed by the L-tryptophan hydroxylase-catalyzed hydroxylation of L-tryptophan back to THB, thus allowing for a more cost-efficient 5HTP synthesis. In one embodiment, the recombinant host cell comprises enzymes of both the first and second THB pathways. Non-limiting and exemplary nucleic acids encoding enzymes of the first and second THB pathways for use in aspects and embodiments of the present invention include those shown in Table 1 of WO 2015/032911 A1, which is hereby specifically incorporated by reference, including the actual amino acid sequences referred to in the table as SEQ ID numbers.

Most types of host cells (e.g., mammalian host cells, yeast host cells such as $S.\ cerevisiae$, bacteria such as $E.\ coli$, etc.) are capable of producing and regenerating acetyl-CoA and SAM; the cofactors for AANAT and ASMT, respectively.

AcCoA serves as a metabolic cofactor in the AANAT reaction, but is also part of other, endogenous pathways in, e.g., microbial cells.

SAM is a principal methyl donor in various intracellular transmethylation reactions. It is synthesized in the cell through SAM synthetase from methionine and ATP, and natively generated through the SAM cycle, which consists of a methyl transferase, an S-adenosyl-L-homocysteine hydrolase, a folate transferase, and an S-adenosyl-methionine synthetase (Lee et al., Korean J. Chem. Eng. 2010, 27, 587-589). Accordingly, in the ASMT-catalyzed, last reaction in the production of melatonin from L-tryptophan, N-acetylserotonin and SAM are converted to melatonin and SAH. SAH can then be recycled back to SAM via the SAM-cycle in microbial cells where the S-adenosyl-L-methionine cycle is native (or exogenously added) and constitutively expressed, such as, e.g., in $E.\ coli$. The enzymes of such native pathways can also, in needed, be upregulated or expressed from an exogenously introduced vector, using well-known recombinant techniques known in text books referenced elsewhere herein. Non-limiting and exemplary nucleic acids encoding enzymes of the SAM cycle for use in aspects and embodiments of the present invention include those shown in Table 1 of WO 2015/032911 A1, which is hereby specifically incorporated by reference, including the actual amino acid sequences referred to in the table as SEQ ID numbers.

The recombinant host cell is typically prepared by introducing into the host cell, typically via transformation, one or more vectors according to any preceding embodiment, using standard methods known in the art and cited elsewhere herein. The introduction of a vector into a bacterial host cell may, for instance, be effected by protoplast transformation (see, e.g., Chang and Cohen, 1979, Molecular General Genetics 168: 111-115), using competent cells (see, e.g., Young and Spizizen, 1961, Journal of Bacteriology 81: 823-829, or Dubnau and Davidoff-Abelson, 1971, Journal of Molecular Biology 56: 209-221), electroporation (see, e.g., Shigekawa and Dower, 1988, Biotechniques 6: 742-751), or conjugation (see, e.g., Koehler and Thorne, 1987, Journal of Bacteriology 169: 5771-5278).

As described above, the vector, once introduced, may be maintained as a chromosomal integrant or as a self-replicating extra-chromosomal vector.

Preferably, for transformation of an $E.\ coli$ or other bacterial host cell, the vectors are designed as follows: A lac promoter is used to control the expressions of a gene or an artificial operon containing up to three genes connected with a linker sequence, in order to express the genes at a suitable level so that the introduction of heterologous genes/pathways do not overdraw substrates or energy in the host cell. In one particular embodiment, the recombinant microbial cell, preferably derived from a bacterial cell, is transformed according to a strategy outlined in the Examples.

Preferably, for transformation of a yeast host cell such as $S.\ cerevisiae$, the heterologous genes are integrated onto chromosome using a homologous recombination based method (Mikkelsen et al., 2012). As compared with gene expression based on plasmids, the chromosomal integrated genes can be expressed with higher fidelity and resulted in better protein translation, in particular for multiple gene co-expression systems.

The transformation can be confirmed using methods well known in the art. Such methods include, for example, nucleic acid analysis such as Northern blots or polymerase chain reaction (PCR) amplification of mRNA, or immunoblotting for expression of gene products, or other suitable analytical methods to test the expression of an introduced nucleic acid sequence or its corresponding gene product, including those referred to above and relating to measurement of 5HTP production. Expression levels can further be optimized to obtain sufficient expression using methods well known in the art and as disclosed herein.

In one embodiment, the recombinant host cell has been modified so as to downregulate or delete a native gene encoding a cyclopropane fatty acyl phospholipid synthase. As shown in Example 1, *E. coli* cells carrying melatonin production pathway genes stopped melatonin production when mutations occurred in the cfa gene, using a methyltransferase selection system. Without being limited to theory, downregulating or deleting a gene corresponding to the cfa gene in a microbial host cell into which a biosynthetic pathway for melatonin-production according to FIG. 1 has been introduced, improves SAM availability to ASMT, thus improving the yield of melatonin. The amino acid sequence of the Cfa protein and the location of the cfa gene in the *E. coli* genome is known in the art (see NCBI Reference Sequence: NP_416178.1 and references cited therein). Orthologs to the cfa gene in *E. coli* exist in, e.g., *C. glutamicum* ATCC 13032 (cma).

In a preferred embodiment, the host cell is a microbial cell. The microbial host cell for use in the present invention is typically unicellular and can be, for example, a bacterial cell, a yeast host cell, a filamentous fungal cell, or an algeal cell. Examples of suitable host cell genera include, but are not limited to, *Acinetobacter, Agrobacterium, Alcaligenes, Anabaena, Aspergillus, Bacillus, Bifidobacterium, Brevibacterium, Candida, Chlorobium, Chromatium, Corynebacteria, Cytophaga, Deinococcus, Enterococcus, Erwinia, Erythrobacter, Escherichia, Flavobacterium, Hansenula, Klebsiella, Lactobacillus, Methanobacterium, Methylobacter, Methylococcus, Methylocystis, Methylomicrobium, Methylomonas, Methylosinus, Mycobacterium, Myxococcus, Pantoea, Phaffia, Pichia, Pseudomonas, Rhodobacter, Rhodococcus, Saccharomyces, Salmonella, Sphingomonas, Streptococcus, Streptomyces, Synechococcus, Synechocystis, Thiobacillus, Trichoderma, Yarrowia* and *Zymomonas*.

In one embodiment, the host cell is bacterial cell, e.g., an *Escherichia* cell such as an *Escherichia coli* cell; a *Bacillus* cell such as a *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis,* or a *Bacillus thuringiensis* cell; or a *Streptomyces* cell such as a *Streptomyces lividans* or *Streptomyces murinus* cell. In a particular embodiment, the recombinant microbial cell is derived from cell of the *Escherichia* genus, such as an *Escherichia coli* cell. In another particular embodiment, the host cell is of an *E. coli* strain selected from the group consisting of K12.DH1 (Proc. Natl. Acad. Sci. USA, volume 60, 160 (1968)), JM101, JM103 (Nucleic Acids Research (1981), 9, 309), JA221 (J. Mol. Biol. (1978), 120, 517), HB101 (J. Mol. Biol. (1969), 41, 459) and C600 (Genetics, (1954), 39, 440).

In one embodiment, the host cell is a fungal cell, such as, e.g., a yeast cell. Exemplary yeast cells include *Candida, Hansenula, Kluyveromyces, Pichia, Saccharomyces, Schizosaccharomyces* and *Yarrowia* cells. In a particular embodiment, the host cell is an *S. cerevisiae* cell. In another particular embodiment, the host cell is of an *S. cerevisie* strain selected from the group consisting of *S. cerevisiae* KA31, AH22, AH22R-, NA87-11A, DKD-5D and 20B-12, *S. pombe* NCYC1913 and NCYC2036 and *Pichia pastoris* KM71.

In one embodiment, the recombinant microbial is derived from an *Escherichia, Saccharomyces*, a *Schizosaccharomyces*, a *Corynebacterium*, a *Bacillus* or a *Streptomyces* cell.

Production of Melatonin

The invention also provides a method of producing melatonin, comprising culturing the recombinant microbial cell of any preceding aspect or embodiment in a medium comprising a carbon source. The desired compound can then optionally be isolated or retrieved from the medium, and optionally further purified. Importantly, using a recombinant microbial cell according to the invention, the method can be carried out without adding L-tryptophan, THB, or both, to the medium.

Also provided is a method of preparing a composition comprising melatonin, comprising culturing the recombinant microbial cell of any preceding aspect or embodiment, isolating and purifying the compound, and adding any excipients to obtain the composition.

Suitable carbon sources include carbohydrates such as monosaccharides, oligosaccharides and polysaccharides. As used herein, "monosaccharide" denotes a single unit of the general chemical formula $C_x(H2O)_y$, without glycosidic connection to other such units, and includes glucose, fructose, xylose, arabinose, galactose and mannose. "Oligosaccharides" are compounds in which monosaccharide units are joined by glycosidic linkages, and include sucrose and lactose. According to the number of units, oligosacchardies are called disaccharides, trisaccharides, tetrasaccharides, pentasaccharides etc. The borderline with polysaccharides cannot be drawn strictly; however the term "oligosaccharide" is commonly used to refer to a defined structure as opposed to a polymer of unspecified length or a homologous mixture. "Polysaccharides" is the name given to a macromolecule consisting of a large number of monosaccharide residues joined to each other by glycosidic linkages, and includes starch, lignocellulose, cellulose, hemicellulose, glycogen, xylan, glucuronoxylan, arabinoxylan, arabinogalactan, glucomannan, xyloglucan, and galactomannan. Other suitable carbon sources include acetate, glycerol, pyruvate and gluconate. In one embodiment, the carbon source is selected from the group consisting of glucose, fructose, sucrose, xylose, mannose, galactose, rhamnose, arabinose, fatty acids, glycerine, glycerol, acetate, pyruvate, gluconate, starch, glycogen, amylopectin, amylose, cellulose, cellulose acetate, cellulose nitrate, hemicellulose, xylan, glucuronoxylan, arabinoxylan, glucomannan, xyloglucan, lignin, and lignocellulose. In one embodiment, the carbon source comprises one or more of lignocellulose and glycerol. In one embodiment, the carbon source is a simple carbon source such as glucose, xylose, fructose, arabinose, galactose, mannose, glycerol, acetate, or a mixture of any thereof.

The culture conditions are adapted to the recombinant microbial host cell, and can be optimized to maximize production or melatonin or a related compound by varying culture conditions and media components as is well-known in the art.

For a recombinant *Escherichia coli* cell, exemplary media include LB medium and M9 medium (Miller, Journal of Experiments in Molecular Genetics, 431-433, Cold Spring Harbor Laboratory, New York, 1972), optionally supplemented with one or more amino acids. When an inducible promoter is used, the inductor can also be added to the medium. Examples include the lac promoter, which can be activated by adding isopropyl-beta-thiogalacto-pyranoside (IPTG) and the GAL/BAD promoter, in which case galactose/arabinose can be added. The culturing can be carried out a temperature of about 10 to 40° C. for about 3 to 72 hours, if desired, with aeration or stirring.

For a recombinant *Bacillus* cell, culturing can be carried out in a known medium at about 30 to 40° C. for about 6 to 40 hours, if desired with aeration and stirring. With regard to the medium, known ones may be used. For example, pre-culture can be carried out in an LB medium and then the main culture using an NU medium.

For a recombinant yeast cell, Burkholder minimum medium (Bostian, K. L., et al. Proc. Natl. Acad. Sci. USA, volume 77, 4505 (1980)), SD medium containing 0.5% of Casamino acid (Bitter, G. A., et al., Proc. Natl. Acad. Sci. USA, volume 81, 5330 (1984), and Delft medium (Verduyn et al., Yeast 1992, 8, 501-517) can be used. The pH is preferably adjusted to about 5-8. For example, a synthetic medium may contain, per litre: (NH4)2SO4, 5 g; KH2PO4, 3 g; MgSO4.7H2O, 0.5 g; EDTA, 15 mg; ZnSO4.7H2O, 4.5 mg; CoCl2.6H2O, 0.3 mg; MnCl2.4H2O, 1 mg; CuSO4 5H2O, 0.3 mg; CaCl2.2H2O, 4.5 mg; FeSO4.7H2O, 3 mg; NaMoO4.2H2O, 0.4 mg; H3BO3, 1 mg-KI, 0.1 mg; and 0.025 ml silicone antifoam (BDH). Filter-sterilized vitamins can be added after heat sterilization (120° C.), to final concentrations per litre of: biotin, 0.05 mg; calcium pantothenate, 1 mg; nicotinic acid, 1 mg; inositol, 25 mg; thiamine HCl, 1 mg; pyridoxine HCl, 1 mg; and para-aminobenzoic acid, 0.2 mg. The medium can then be adjusted to pH6 with KOH. Culturing is preferably carried out at about 20 to about 40° C., for about 24 to 84 hours, if desired with aeration or stirring.

In one embodiment, no L-tryptophan is added to the medium. In another embodiment, no L-tryptophan or THB is added to the medium, so that the production of melatonin or its precursors or related compounds rely on substrates biosynthesized in the recombinant host cell.

Using the method for producing melatonin, a melatonin yield of at least about 0.5%, such as at least about 1%, such as at least 5%, such as at least 10%, such as at least 20%, at least 30%, at least 40%, at least 50%, at least 60%, at least 70%, at least 80% or at least 90% of the theoretically possible yield can be obtained from a suitable carbon source, such as glucose.

Isolation of melatonin from the cell culture can be achieved, e.g., by separating the compound from the cells using a membrane, using, for example, centrifugation or filtration methods. The product-containing supernatant is then collected. Further purification of the desired compound can then be carried out using known methods, such as, e.g., salting out and solvent precipitation; molecular-weight-based separation methods such as dialysis, ultrafiltration, and gel filtration; charge-based separation methods such as ion-exchange chromatography; and methods based on differences in hydrophobicity, such as reversed-phase HPLC; and the like. In one embodiment, ion-exchange chromatography is used for purification of serotonin. In one embodiment, reverse-phase chromatography is used for separation and/or purification of melatonin. An exemplary method for purification of these indolamines using reversed-phase chromatography is described in Harumi et al., (1996) (J Chromatogr B 675:152-156).

Once a sufficiently pure preparation has been achieved, suitable excipients, stabilizers can optionally be added and the resulting preparation incorporated in a composition for use in preparing a product such as, e.g., a dietary supplement, a pharmaceutical, a cosmeceutical, or a nutraceutical. For a dietary supplement comprising melatonin, each serving can contain, e.g., from about 0.01 mg to about 100 mg melatonin, such as from about 0.1 mg to about 10 mg, or about 1-5 mg, such as 2-3 mg. Emulsifiers may be added for stability of the final product. Examples of suitable emulsifiers include, but are not limited to, lecithin (e.g., from egg or soy), and/or mono- and di-glycerides. Other emulsifiers are readily apparent to the skilled artisan and selection of suitable emulsifier(s) will depend, in part, upon the formulation and final product. Preservatives may also be added to the nutritional supplement to extend product shelf life. Preferably, preservatives such as potassium sorbate, sodium sorbate, potassium benzoate, sodium benzoate or calcium disodium EDTA are used.

EXAMPLE 1

Media and Growth Conditions

All strains were maintained at 37° C. in LB (Lennox) Broth (Sigma-Aldrich), 2×YT or M9 minimum media containing 1×M9 minimal salts (BD Difco™), 2 mM MgSO$_4$, 100 µM CaCl$_2$, 500-fold diluted trace minerals (10 g/l FeCl$_3$.6H$_2$O, 2 g/l ZnSO$_4$.7H$_2$O, 0.4 g/l CuCl$_2$.2H$_2$O, 1 g/l MnSO$_4$.H$_2$O, 0.6 g/l CoCl$_2$.6H$_2$O, and 1.6 mM EDTA, pH 8.0), 1× ATCC® Vitamin Supplement (ATCC MD-VS™), and 0.2% glucose (w/v).

Plasmids

The wild type human ASMT (hsASMT), codon-optimized for *E. coli* expression, was harbored in the pHM18 plasmid of a P15A origin. The A258E, G260D and T272A variants of hsASMT were constructed by site-directed mutagenesis and were harbored in pHM64, pHM65 and pHM66 derived from pHM18. All hsASMT variants were expressed under a strong Ptrc promoter.

Metabolite Analysis by LC-MS

LC-MS data was collected on OrbiTrap Fusion High Resolution Mass Spectrometer system coupled with an Ultimate 3000 UHPLC pump (Thermo, San Jose Calif.). Samples were held in the autosampler at a temperature of 10.0° C. during the analysis. 1 µL Injections of the sample were made onto a Thermo HyperSil Gold PFP HPLC column, with a 3 um particle size, 2.1 mm i.d. and 150 mm long. The column was held at a temperature of 35.0° C. The solvent system used was Solvent A "Water with 0.1% formic acid" and Solvent B "Acetonitrile with 0.1% formic". The Flow Rate was 1.000 ml/min with an Initial Solvent composition of % A=95, % B=5 held until 0.50 min, the solvent composition was then changed following a Linear Gradient until it reached % A=70.0 and % B=30.0 at 1.50 min. The solvent composition was then changed following a Linear Gradient until it reached % A=5.0 and % B=95.0 at 2.00 min This was held until 2.50 min when the solvent was returned to the initial conditions and the column was re-equilibrated until 3.00 min. The first 0.25 min of the run was diverted to waste using the divert valve, following which the column eluent flowed directly into the Heated ESI probe of the MS which was held at 325° C. and a voltage of 3500 V. Data was collected in positive ion mode over the mass range 50 to 1000 m/z at a resolution of 15.000. The other MS settings were as follows, Sheath Gas Flow Rate of 60 units, Cone Gas Flow Rate of 20 units Cone Temp was 275° C.

hsASMT Variants Characterization

Three point mutations of hsASMT were identified using a methyltransferase engineering platform. The mutations were A258E, G260D and T272A, respectively. All three mutations were re-introduced onto the wild-type hsASMT gene yielding pHM64, pHM65 and pHM66 derived from the wild-type hsASMT carrying pHM18. The resulting plasmids were transformed into E. coli. The transformed cells were subjected to an in vivo turnover activity assay whereas cells were grown in M9 medium supplemented with 200 mg/l of acetylserotonin at 37° C. following by removing cell broth at various time points for exo-metabolites analysis and turnover activity calculations. Turnover activity of the mutants was benchmarked against wild-type hsASMT and results indicated all mutational changes led to an increase in acetylserotonin turnover at 2.6-fold, 2.3-fold and 1.6-fold, respectively (FIG. 2).

Structural Analysis of hsASMT Variants

Wild-type human ASMT comprises 345 amino acids. Botros et al. (2013) reported two structural states of hsASMT with either s-adenosylmethionine (SAM) bound (PDB: 4a6d) or both SAM and N-acetylserotonin bound (PDB: 4a6e). Structural analysis showed that the hsASMT protein consisted of 16 α-helices and the A258, G260 and T272 residues played a role in positioning the 14$^{th}$ helix. The 14$^{th}$ helix, D259-H271, locates at a strategic position whereas it guards the entry opening of the SAM cofactor via interactions with the adjacent residues (including P241-Y248 and T307-Q310). In particular, without being limited to theory, the three beneficial mutations identified may each have resulted in a widening of the SAM entry opening. For example, a mutation of A258 to Glu (E) could result in a repulsive hydrophilic interaction with E308, hence "pushing" the helix away for enlarged opening. In contrast, the T272A mutation could relax the hydrophobic interaction between L242-E244 so that the helix becomes more flexible. Finally, the mutation of G260 to Asp (D) apparently interacts with D259, the first amino acid of the helix-14. The structural analysis showed that the identified mutations regulated SAM entry and possibly affected affinity of hsASMT towards SAM (i.e. a low $K_m$ for SAM). Furthermore, sequence alignment of 6 functional ASMTs showed that the identified residues were less conserved throughout the course of the evolution than the surrounding residues, suggesting a flexibility to changes in individual organisms to adapt their own cellular SAM environment (FIG. 3).

Identifying Cfa as a Native SAM Sink

Using the methyltransferase engineering platform, non-melatonin producers with cfa mutations were identified. The specific mutations occurred either within the initial coding region of cfa (e.g. C5S or C5Y) or its promoter region, indicating changes in expression of the cfa gene. Since the cfa gene encodes for a SAM-dependent fatty acid synthase, it was concluded that Cfa was the SAM sink for the non-melatonin producers.

LIST OF REFERENCES

Botros et al., J Pineal Res 2013; 54:46-57
Kang et al., J. Pineal Res. 2011; 50:304-309
Byeon et al., J. Pineal Res 2016; 60:65-73
UniProtKB-P46597 (ASMT_HUMAN); accessed on 13 Apr. 2016
WO 2013/127914 A1, WO 2013/127915 A1 and WO 2015/032911 A1 (Danmarks Tekniske Universitet)
US 2014/134689 AA (University of California)
WO 2007/052166 (Institut Pasteur)
WO 02/06337 (Shanghai Biowindow Gene Development Inc.)
UniProtKB database entry AOA096MY35
UniProtKB database entry AOA091UVP6
UniProt database entry AOA091GD70
EBI accession no. EMBL:KFQ94517.1

The invention claimed is:

1. A nucleic acid encoding a variant of *Homo sapiens* acetylserotonin O-methyltransferase (ASMT), the variant having at least 98% sequence identity to the polypeptide of SEQ ID NO: 1 and comprising one or more mutations in the segment corresponding to residues 258 to 272 in the polypeptide of SEQ ID NO: 1, wherein the variant has an increased catalytic activity in converting N-acetylserotonin to melatonin as compared to the polypeptide of SEQ ID NO: 1 and comprises a mutation in one or more residues corresponding to residues 258, 260, or 272 in the polypeptide of SEQ ID NO: 1.

2. The nucleic acid of claim 1, wherein the variant has at least 50% increased catalytic activity in converting N-acetylserotonin to melatonin as compared to the polypeptide of SEQ ID NO: 1.

3. The nucleic acid of claim 2, wherein the variant has at least 99% sequence identity to the polypeptide of SEQ ID NO: 1.

4. The nucleic acid of claim 3, wherein the variant comprises a mutation in the residue corresponding to residue 258 in the polypeptide of SEQ ID NO: 1.

5. The nucleic acid of claim 2, wherein the mutation is an amino acid substitution corresponding to an amino acid substitution in the polypeptide of SEQ ID NO: 1 selected from the group consisting of A258E, G260D, G260N, G260L, G260I, T272A and T272G.

6. A nucleic acid encoding a variant of *Homo sapiens* ASMT, the variant having at least 92% sequence identity to the polypeptide of SEQ ID NO: 1 and comprising one or more mutations in the segment corresponding to residues 258 to 272 in the polypeptide of SEQ ID NO: 1, wherein the variant has an increased catalytic activity in converting N-acetylserotonin to melatonin as compared to the polypeptide of SEQ ID NO: 1 and comprises an amino acid substitution in one or more residues corresponding to residues 258, 260, and 272 in the polypeptide of SEQ ID NO: 1, wherein the amino acid substitutions correspond to A258E, G260D, or T272A in the polypeptide of SEQ ID NO: 1.

7. The nucleic acid of claim 6, wherein the variant has at least 50% increased catalytic activity in converting N-acetylserotonin to melatonin as compared to the polypeptide of SEQ ID NO: 1.

8. The nucleic acid of claim 7, wherein the variant has at least 98% sequence identity to the polypeptide of SEQ ID NO: 1.

9. The nucleic acid of claim 8, wherein the variant has at least 99% sequence identity to the polypeptide of SEQ ID NO: 1 and comprises an amino acid substitution corresponding to A258E in the polypeptide of SEQ ID NO: 1.

10. A recombinant host cell comprising a nucleic acid encoding a variant of *Homo sapiens* acetylserotonin O-methyltransferase (ASMT), the variant having at least 98% sequence identity to the polypeptide of SEQ ID NO: 1 and comprising one or more mutations in the segment corresponding to residues 258 to 272 in the polypeptide of SEQ ID NO: 1, wherein the variant has an increased catalytic activity in converting N-acetylserotonin to melatonin as compared to the polypeptide of SEQ ID NO: 1 and comprises a mutation in one or more residues corresponding to residues 258, 260, or 272 in the polypeptide of SEQ ID NO: 1.

11. A recombinant host cell comprising a nucleic acid encoding a variant of *Homo sapiens* ASMT, the variant having at least 92% sequence identity to the polypeptide of SEQ ID NO: 1 and comprising one or more mutations in the segment corresponding to residues 258 to 272 in the polypeptide of SEQ ID NO: 1, wherein the variant has an increased catalytic activity in converting N-acetylserotonin to melatonin as compared to the polypeptide of SEQ ID NO: 1 and comprises an amino acid substitution in one or more residues corresponding to residues 258, 260, and 272 in the polypeptide of SEQ ID NO: 1, wherein the amino acid substitutions correspond to A258E, G260D, or T272A in the polypeptide of SEQ ID NO: 1.

12. A recombinant host cell comprising a nucleic acid encoding a variant of *Homo sapiens* acetylserotonin O-methyltransferase (ASMT), the variant having at least 99% sequence identity to the polypeptide of SEQ ID NO: 1 and comprises an amino acid substitution corresponding to A258E in the polypeptide of SEQ ID NO: 1, said variant having at least 50% increased catalytic activity in converting N-acetylserotonin to melatonin as compared to the polypeptide of SEQ ID NO: 1.

13. The recombinant host cell of claim 12, wherein the nucleic acid is comprised in a vector, wherein the nucleic acid sequence is optionally operably linked to one or more expression control sequences.

14. The recombinant host cell of claim 12, wherein the nucleic acid is integrated into the genome.

15. The recombinant host cell of claim 13, which is a mammalian cell, a bacterial cell, a yeast cell, a filamentous fungal cell or an algal cell.

16. The recombinant host cell of claim 15, which is an *E. coli* cell.

17. The recombinant cell of claim 16, comprising a heterologous biosynthetic pathway for producing N-acetylserotonin comprising an L-tryptophan hydroxylase, a 5HTP decarboxylase and a serotonin acetyltransferase, and a native pathway for recycling 5-adenosyl-L-homocysteine (SAH) into S-adenosyl-L-methionine (SAM),
wherein said L-tryptophan hydroxylase is selected from the group consisting of *Oryctolagus cuniculus* TPH1, *Homo sapiens* TPH1, *Homo sapiens* TPH2, a *Gallus gallus* L-tryptophan hydroxylase, a *Mus musculus* L-tryptophan hydroxylase, an *Equus caballus* L-tryptophan hydroxylase, a *Schistosoma mansoni* L-tryptophan hydroxylase, a *Homo sapiens* TPH2 comprising SEQ ID NO: 17, a *Homo sapiens* TPH2 comprising SEQ ID NO: 18, a *Homo sapiens* TPH2 comprising SEQ ID NO: 19, and a *Homo sapiens* TPH2 comprising SEQ ID NO: 20;
wherein said 5HTP decarboxylase is selected from the group consisting of an *Acidobacterium capsulatum* 5HTP decarboxylase, a *Rattus norvegicus* 5HTP decarboxylase, a *Sus scrofa* 5HTP decarboxylase, a *Homo sapiens* 5HTP decarboxylase, a *Capsicum annuum* 5HTP decarboxylase, a *Drosophila caribiana* 5HTP decarboxylase, a *Maricaulis maris* 5HTP decarboxylase, an *Oryza sativa* subsp. *Japonica* 5HTP decarboxylase, a *Pseudomonas putida* S16 5HTP decarboxylase, and a *Catharanthus roseus* 5HTP decarboxylase; and
wherein said serotonin acetyltransferase is selected from the group consisting of a *Chlamydomonas reinhardtii* serotonin acetyltransferase, a *Bos taurus* serotonin acetyltransferase, a *Gallus gallus* serotonin acetyltransferase, a *Homo sapiens* serotonin acetyltransferase, a *Mus musculus* serotonin acetyltransferase, an *Oryctolagus cuniculus* serotonin acetyltransferase, and an *Ovis aries* serotonin acetyltransferase.

18. The recombinant host cell of claim 17, comprising a mutation in an endogenous gene encoding a cyclopropane fatty acyl phospholipid synthase to reduce or eliminate the expression of said gene.

19. A method of producing melatonin, comprising culturing the recombinant host cell of claim 17 in a medium comprising a carbon source, and, optionally, isolating melatonin.

* * * * *

UNITED STATES PATENT AND TRADEMARK OFFICE
CERTIFICATE OF CORRECTION

PATENT NO. : 11,332,767 B2
APPLICATION NO. : 17/109715
DATED : May 17, 2022
INVENTOR(S) : Hao Luo

It is certified that error appears in the above-identified patent and that said Letters Patent is hereby corrected as shown below:

In the Specification

Column 12, in TABLE 1, change "Rattus norwegicus" to — Rattus norvegicus —

Column 23, Line 21, change "s-adenosylmethionine" to — S-adenosylmethionine —

In the Claims

Column 64, Claim 17, Line 15, after "The recombinant" insert -- host --

Column 64, Claim 17, Line 19, change "5-adenosyl-L-homocysteine" to — S-adenosyl-L-homocysteine —

Signed and Sealed this
Third Day of January, 2023

Katherine Kelly Vidal
*Director of the United States Patent and Trademark Office*

SEQUENCE LISTING

<160> NUMBER OF SEQ ID NOS: 20

<210> SEQ ID NO 1
<211> LENGTH: 345
<212> TYPE: PRT
<213> ORGANISM: Homo sapiens

<400> SEQUENCE: 1

```
Met Gly Ser Ser Glu Asp Gln Ala Tyr Arg Leu Leu Asn Asp Tyr Ala
1               5                   10                  15

Asn Gly Phe Met Val Ser Gln Val Leu Phe Ala Ala Cys Glu Leu Gly
            20                  25                  30

Val Phe Asp Leu Leu Ala Glu Ala Pro Gly Pro Leu Asp Val Ala Ala
        35                  40                  45

Val Ala Ala Gly Val Arg Ala Ser Ala His Gly Thr Glu Leu Leu Leu
    50                  55                  60

Asp Ile Cys Val Ser Leu Lys Leu Leu Lys Val Glu Thr Arg Gly Gly
65                  70                  75                  80

Lys Ala Phe Tyr Arg Asn Thr Glu Leu Ser Ser Asp Tyr Leu Thr Thr
                85                  90                  95

Val Ser Pro Thr Ser Gln Cys Ser Met Leu Lys Tyr Met Gly Arg Thr
            100                 105                 110

Ser Tyr Arg Cys Trp Gly His Leu Ala Asp Ala Val Arg Glu Gly Arg
```

```
            115                 120                 125
Asn Gln Tyr Leu Glu Thr Phe Gly Val Pro Ala Glu Glu Leu Phe Thr
        130                 135                 140
Ala Ile Tyr Arg Ser Glu Gly Glu Arg Leu Gln Phe Met Gln Ala Leu
145                 150                 155                 160
Gln Glu Val Trp Ser Val Asn Gly Arg Ser Val Leu Thr Ala Phe Asp
                165                 170                 175
Leu Ser Val Phe Pro Leu Met Cys Asp Leu Gly Gly Gly Ala Gly Ala
                180                 185                 190
Leu Ala Lys Glu Cys Met Ser Leu Tyr Pro Gly Cys Lys Ile Thr Val
            195                 200                 205
Phe Asp Ile Pro Glu Val Val Trp Thr Ala Lys Gln His Phe Ser Phe
210                 215                 220
Gln Glu Glu Glu Gln Ile Asp Phe Gln Glu Gly Asp Phe Phe Lys Asp
225                 230                 235                 240
Pro Leu Pro Glu Ala Asp Leu Tyr Ile Leu Ala Arg Val Leu His Asp
                245                 250                 255
Trp Ala Asp Gly Lys Cys Ser His Leu Leu Glu Arg Ile Tyr His Thr
                260                 265                 270
Cys Lys Pro Gly Gly Gly Ile Leu Val Ile Glu Ser Leu Leu Asp Glu
            275                 280                 285
Asp Arg Arg Gly Pro Leu Leu Thr Gln Leu Tyr Ser Leu Asn Met Leu
        290                 295                 300
Val Gln Thr Glu Gly Gln Glu Arg Thr Pro Thr His Tyr His Met Leu
305                 310                 315                 320
Leu Ser Ser Ala Gly Phe Arg Asp Phe Gln Phe Lys Lys Thr Gly Ala
                325                 330                 335
Ile Tyr Asp Ala Ile Leu Ala Arg Lys
                340                 345

<210> SEQ ID NO 2
<211> LENGTH: 361
<212> TYPE: PRT
<213> ORGANISM: Ocimicum basilicum

<400> SEQUENCE: 2

Met Ser Ser Thr Ala Asn Asn Pro Gln Ile Asn Ser Asp Glu Glu
1               5                   10                  15
Asn Phe Leu Phe Ala Met Gln Leu Ala Ser Ala Ser Val Leu Pro Met
                20                  25                  30
Val Leu Lys Ser Ala Ile Glu Leu Asp Leu Leu Glu Leu Ile Lys Lys
            35                  40                  45
Ala Gly Ala Gly Ala Phe Val Ser Pro Ala Glu Leu Ala Ala Gln Leu
        50                  55                  60
Leu Thr Thr Asn Ala Glu Ala His Val Met Leu Asp Arg Ile Leu Arg
65                  70                  75                  80
Leu Leu Thr Ser Tyr Ala Ile Leu Glu Cys Arg Leu Lys Thr Leu Pro
                85                  90                  95
Asp Gly Gly Val Gln Arg Leu Tyr Gly Leu Ala Pro Val Cys Lys Phe
                100                 105                 110
Leu Thr Lys Asn Glu Asp Gly Val Ser Met Ala Pro Leu Ala Leu Met
            115                 120                 125
Asn Gln Asp Lys Val Leu Met Glu Ser Trp Tyr His Leu Lys Asp Ala
        130                 135                 140
```

```
Val Leu Asp Gly Gly Ile Pro Phe Asn Lys Ala Tyr Gly Met Thr Ala
145                 150                 155                 160

Phe Glu Tyr His Gly Thr Asp Pro Arg Phe Asn Lys Val Phe Asn Gln
            165                 170                 175

Gly Met Ser Asn His Ser Thr Ile Thr Met Lys Lys Ile Leu Glu Thr
        180                 185                 190

Tyr Thr Gly Phe Asp Gly Leu Lys Thr Val Val Asp Val Gly Gly Gly
    195                 200                 205

Thr Gly Ala Thr Leu Asn Met Ile Ile Ser Lys Tyr Pro Ser Ile Lys
210                 215                 220

Gly Ile Asn Phe Asp Leu Pro His Val Val Glu Asp Ala Pro Ser Tyr
225                 230                 235                 240

Pro Gly Val Glu His Val Gly Gly Asp Met Phe Val Ser Val Pro Lys
            245                 250                 255

Gly Asp Ala Ile Phe Met Lys Trp Ile Cys His Asp Trp Ser Asp Ala
        260                 265                 270

His Cys Val Lys Phe Leu Lys Lys Cys Tyr Glu Ala Leu Pro Glu Asn
    275                 280                 285

Gly Lys Val Ile Leu Ala Glu Cys Val Leu Pro Glu Ala Pro Asp Thr
290                 295                 300

Gly Leu Ala Thr Lys Asn Val Val His Ile Asp Val Ile Met Leu Ala
305                 310                 315                 320

His Asn Pro Gly Gly Lys Glu Arg Thr Glu Lys Glu Phe Gln Val Leu
            325                 330                 335

Ala Lys Ala Ser Gly Phe Lys Gln Phe Asn Lys Val Cys Cys Ala Tyr
        340                 345                 350

Asn Ser Trp Ile Met Glu Leu Leu Lys
    355                 360

<210> SEQ ID NO 3
<211> LENGTH: 345
<212> TYPE: PRT
<213> ORGANISM: Bos taurus

<400> SEQUENCE: 3

Met Cys Ser Gln Glu Gly Glu Gly Tyr Ser Leu Leu Lys Glu Tyr Ala
1               5                   10                  15

Asn Gly Phe Met Val Ser Gln Val Leu Phe Ala Ala Cys Glu Leu Gly
            20                  25                  30

Val Phe Glu Leu Leu Ala Glu Ala Leu Glu Pro Leu Asp Ser Ala Ala
        35                  40                  45

Val Ser Ser His Leu Gly Ser Ser Pro Gln Gly Thr Glu Leu Leu Leu
    50                  55                  60

Asn Thr Cys Val Ser Leu Lys Leu Leu Gln Ala Asp Val Arg Gly Gly
65                  70                  75                  80

Lys Ala Val Tyr Ala Asn Thr Glu Leu Ala Ser Thr Tyr Leu Val Arg
            85                  90                  95

Gly Ser Pro Arg Ser Gln Arg Asp Met Leu Leu Tyr Ala Gly Arg Thr
        100                 105                 110

Ala Tyr Val Cys Trp Arg His Leu Ala Glu Ala Val Arg Glu Gly Arg
    115                 120                 125

Asn Gln Tyr Leu Lys Ala Phe Gly Ile Pro Ser Glu Glu Leu Phe Ser
130                 135                 140

Ala Ile Tyr Arg Ser Glu Asp Glu Arg Leu Gln Phe Met Gln Gly Leu
145                 150                 155                 160
```

-continued

```
Gln Asp Val Trp Arg Leu Glu Gly Ala Thr Val Leu Ala Ala Phe Asp
                165                 170                 175

Leu Ser Pro Phe Pro Leu Ile Cys Asp Leu Gly Gly Gly Ser Gly Ala
            180                 185                 190

Leu Ala Lys Ala Cys Val Ser Leu Tyr Pro Gly Cys Arg Ala Ile Val
        195                 200                 205

Phe Asp Ile Pro Gly Val Gln Ile Ala Lys Arg His Phe Ser Ala
    210                 215                 220

Ser Glu Asp Glu Arg Ile Ser Phe His Glu Gly Asp Phe Phe Lys Asp
225                 230                 235                 240

Ala Leu Pro Glu Ala Asp Leu Tyr Ile Leu Ala Arg Val Leu His Asp
                245                 250                 255

Trp Thr Asp Ala Lys Cys Ser His Leu Leu Gln Arg Val Tyr Arg Ala
            260                 265                 270

Cys Arg Thr Gly Gly Gly Ile Leu Val Ile Glu Ser Leu Leu Asp Thr
        275                 280                 285

Asp Gly Arg Gly Pro Leu Thr Thr Leu Leu Tyr Ser Leu Asn Met Leu
    290                 295                 300

Val Gln Thr Glu Gly Arg Glu Arg Thr Pro Ala Glu Tyr Arg Ala Leu
305                 310                 315                 320

Leu Gly Pro Ala Gly Phe Arg Asp Val Arg Cys Arg Arg Thr Gly Gly
                325                 330                 335

Thr Tyr Asp Ala Val Leu Ala Arg Lys
            340                 345

<210> SEQ ID NO 4
<211> LENGTH: 335
<212> TYPE: PRT
<213> ORGANISM: Takifugu rubripes

<400> SEQUENCE: 4

Met Phe Leu Ile Ala His Leu Pro Leu Pro Gln Val Val Phe Ser Ser
1               5                   10                  15

Cys Glu Leu Gly Val Phe Asp Leu Leu Leu Gly Ala Glu Arg Pro Leu
            20                  25                  30

Ser Ala Glu Glu Ile Ser Arg Ala Leu Gly Thr Ser Val Asp Gly Thr
        35                  40                  45

Glu Arg Leu Leu Ala Ala Cys Ser Gly Leu Gln Leu Leu Asn Ile His
    50                  55                  60

Gln Asp Asn Gly Arg Cys Leu Tyr Ser Asn Thr Asp Gln Ala Ser Val
65                  70                  75                  80

Tyr Leu Thr Arg Ser Ser Pro Val Ser Leu Ser Gln Ser Ile Gln Tyr
                85                  90                  95

Ser Ser Arg Thr Ile Tyr Leu Cys Trp His Tyr Leu Thr Asp Ala Val
            100                 105                 110

Arg Glu Gly Arg Asn Gln Tyr Glu Lys Ala Phe Gly Val Asp Ala Gln
        115                 120                 125

Asp Leu Phe Gln Ala Leu Tyr Arg Ser Asp Glu Glu Met Val Lys Phe
    130                 135                 140

Met Gln Leu Met Asn Ser Ile Trp Asn Ile Cys Gly Lys Asp Val Val
145                 150                 155                 160

Thr Ala Phe Asp Leu Ser Pro Phe Lys Thr Ile Cys Asp Leu Gly Gly
                165                 170                 175

Cys Ser Gly Ala Leu Ala Lys Gln Cys Thr Ser Ala Tyr Pro Glu Cys
```

```
                180             185             190
Thr Val Thr Ile Phe Asp Leu Pro Lys Val Arg Thr Ser Arg Glu
            195             200             205
Asn Phe Phe Thr Glu Ala Asn Gln Arg Ile Gly Phe Cys Glu Gly Asp
            210             215             220
Phe Phe Lys Asp Pro Leu Pro Glu Ala Asp Leu Tyr Val Leu Ala Arg
225             230             235             240
Ile Leu His Asp Trp Thr Asp Gln Arg Cys Leu Glu Leu Leu Arg Arg
                245             250             255
Val His Gly Ala Cys Arg Pro Gly Gly Ser Val Leu Leu Val Glu Ala
                260             265             270
Leu Leu Tyr Glu Asp Gly Ser Gly Pro Leu Thr Ala Gln Leu Tyr Ser
            275             280             285
Leu Asn Met Leu Val Gln Thr Glu Gly Arg Glu Arg Ser Ala Ala Gln
            290             295             300
Tyr Ala Ala Leu Leu Thr Ala Ala Gly Phe Ser Asn Val Gln His Arg
305             310             315             320
Phe Thr Gly Lys Ile Tyr Asp Ala Val Leu Ala Arg Lys Glu Ala
                325             330             335

<210> SEQ ID NO 5
<211> LENGTH: 345
<212> TYPE: PRT
<213> ORGANISM: Macaca mulatta

<400> SEQUENCE: 5

Met Gly Ser Ser Gly Asp Asp Gly Tyr Arg Leu Leu Asn Glu Tyr Thr
1               5               10              15
Asn Gly Phe Met Val Ser Gln Val Leu Phe Ala Ala Cys Glu Leu Gly
                20              25              30
Val Phe Asp Leu Leu Ala Glu Ala Pro Gly Pro Leu Asp Val Ala Ala
            35              40              45
Val Ala Ala Gly Val Glu Ala Ser Ser His Gly Thr Glu Leu Leu Leu
            50              55              60
Asp Thr Cys Val Ser Leu Lys Leu Leu Lys Val Glu Thr Arg Ala Gly
65              70              75              80
Lys Ala Phe Tyr Gln Asn Thr Glu Leu Ser Ser Ala Tyr Leu Thr Arg
                85              90              95
Val Ser Pro Thr Ser Gln Cys Asn Leu Leu Lys Tyr Met Gly Arg Thr
                100             105             110
Ser Tyr Gly Cys Trp Gly His Leu Ala Asp Ala Val Arg Glu Gly Lys
            115             120             125
Asn Gln Tyr Leu Gln Thr Phe Gly Val Pro Ala Glu Asp Leu Phe Lys
            130             135             140
Ala Ile Tyr Arg Ser Glu Gly Glu Arg Leu Gln Phe Met Gln Ala Leu
145             150             155             160
Gln Glu Val Trp Ser Val Asn Gly Arg Ser Val Leu Thr Ala Phe Asp
                165             170             175
Leu Ser Gly Phe Pro Leu Met Cys Asp Leu Gly Gly Gly Pro Gly Ala
            180             185             190
Leu Ala Lys Glu Cys Leu Ser Leu Tyr Pro Gly Cys Lys Val Thr Val
            195             200             205
Phe Asp Val Pro Glu Val Val Arg Thr Ala Lys Gln His Phe Ser Phe
210             215             220
```

```
Pro Glu Glu Glu Ile His Leu Gln Glu Gly Asp Phe Phe Lys Asp
225                 230                 235                 240

Pro Leu Pro Glu Ala Asp Leu Tyr Ile Leu Ala Arg Ile Leu His Asp
            245                 250                 255

Trp Ala Asp Gly Lys Cys Ser His Leu Leu Glu Arg Val Tyr His Thr
            260                 265                 270

Cys Lys Pro Gly Gly Gly Ile Leu Val Ile Glu Ser Leu Leu Asp Glu
            275                 280                 285

Asp Arg Arg Gly Pro Leu Leu Thr Gln Leu Tyr Ser Leu Asn Met Leu
            290                 295                 300

Val Gln Thr Glu Gly Gln Glu Arg Thr Pro Thr His Tyr His Met Leu
305                 310                 315                 320

Leu Ser Ser Ala Gly Phe Arg Asp Phe Gln Phe Lys Lys Thr Gly Ala
                325                 330                 335

Ile Tyr Asp Ala Ile Leu Val Arg Lys
            340                 345

<210> SEQ ID NO 6
<211> LENGTH: 345
<212> TYPE: PRT
<213> ORGANISM: Elephantulus edwardii

<400> SEQUENCE: 6

Met Glu Gly Pro Gly Asp Arg Ala Phe Arg Leu Leu Asn Glu Tyr Ser
1               5                   10                  15

Ser Gly Phe Met Val Ser Gln Val Leu Phe Ala Ala Cys Glu Leu Gly
            20                  25                  30

Val Phe Asp Leu Leu Ala Gln Ala Pro Glu Pro Leu Asp Thr Ala Glu
        35                  40                  45

Leu Ala Thr Arg Leu Gly Thr Ser Leu His Gly Thr Glu Leu Leu Leu
    50                  55                  60

Asp Val Cys Ala Ser Leu Glu Leu Leu Thr Val Glu Thr Lys Arg Asn
65                  70                  75                  80

Arg Ala Val Tyr Gln Asn Thr Asp Leu Ser Thr Thr Phe Leu Val Arg
                85                  90                  95

Thr Ser Pro Thr Cys Gln Leu His Met Leu Leu Tyr Leu Ser Arg Thr
            100                 105                 110

Thr Tyr Leu Cys Trp Gly His Leu Ala Ala Ala Val Arg Glu Gly Lys
        115                 120                 125

Asn Gln Tyr Lys Arg Ala Phe Gly Val Pro Ser Glu Gln Leu Phe Thr
130                 135                 140

Ala Ile Tyr Arg Ser Glu Ala Glu Arg Leu Leu Phe Met Arg Gly Leu
145                 150                 155                 160

Ala Glu Ile Trp Ser Val His Gly Val Gly Val Met Thr Ala Phe Asp
                165                 170                 175

Leu Ser Ala Phe Ser Val Ile Cys Asp Leu Gly Gly Ala Ser Gly Ala
            180                 185                 190

Leu Ala Arg Val Cys Ala Ser Leu Tyr Pro Asp Ser Ser Val Leu Val
        195                 200                 205

Leu Glu Val Pro Glu Val Arg Ala Ala Arg Ser Leu Phe Leu Ser
    210                 215                 220

Thr Val Glu Ala Pro Val Ser Phe Arg Glu Gly Asp Phe Phe Lys Asp
225                 230                 235                 240

Pro Leu Pro Glu Ala Asp Leu Tyr Ile Leu Ala Arg Val Leu His Asp
            245                 250                 255
```

```
Trp Thr Asp Glu Lys Cys Ser Glu Leu Leu Ala Lys Ile His His Thr
            260                 265                 270

Cys Lys Pro Gly Gly Gly Ile Leu Val Val Ser Val Leu Glu Glu
            275                 280                 285

Asp Arg Arg Gly Pro Leu Thr Thr Gln Leu Tyr Ser Leu Asn Met Leu
            290                 295                 300

Val Gln Thr Glu Gly Arg Glu Arg Thr Pro Ala Glu Tyr Arg Ser Leu
305                 310                 315                 320

Ile Cys Ser Ala Gly Phe Gln Asp Phe Gln Leu Lys Lys Thr Gly Lys
                325                 330                 335

Ile Tyr Asp Val Ile Leu Ala Arg Lys
            340                 345

<210> SEQ ID NO 7
<211> LENGTH: 364
<212> TYPE: PRT
<213> ORGANISM: Oryza sativa

<400> SEQUENCE: 7

Met Ala Gln Asn Val Gln Glu Asn Glu Gln Val Met Ser Thr Glu Asp
1               5                   10                  15

Leu Leu Gln Ala Gln Ile Glu Leu Tyr His His Cys Leu Ala Phe Ile
            20                  25                  30

Lys Ser Met Ala Leu Arg Ala Ala Thr Asp Leu Arg Ile Pro Asp Ala
            35                  40                  45

Ile His Cys Asn Gly Gly Ala Ala Thr Leu Thr Asp Leu Ala Ala His
        50                  55                  60

Val Gly Leu His Pro Thr Lys Leu Ser His Leu Arg Arg Leu Met Arg
65              70                  75                  80

Val Leu Thr Leu Ser Gly Ile Phe Thr Val His Asp Gly Asp Gly Glu
                85                  90                  95

Ala Thr Tyr Thr Leu Thr Arg Val Ser Arg Leu Leu Leu Ser Asp Gly
            100                 105                 110

Val Glu Arg Thr His Gly Leu Ser Gln Met Val Arg Val Phe Val Asn
            115                 120                 125

Pro Val Ala Val Ala Ser Gln Phe Ser Leu His Glu Trp Phe Thr Val
        130                 135                 140

Glu Lys Ala Ala Ala Val Ser Leu Phe Glu Val Ala His Gly Cys Thr
145                 150                 155                 160

Arg Trp Glu Met Ile Ala Asn Asp Ser Lys Asp Gly Ser Met Phe Asn
                165                 170                 175

Ala Gly Met Val Glu Asp Ser Ser Val Ala Met Asp Ile Ile Leu Arg
            180                 185                 190

Lys Ser Ser Asn Val Phe Arg Gly Ile Asn Ser Leu Val Asp Val Gly
            195                 200                 205

Gly Gly Tyr Gly Ala Val Ala Ala Ala Val Val Arg Ala Phe Pro Asp
        210                 215                 220

Ile Lys Cys Thr Val Leu Asp Leu Pro His Ile Val Ala Lys Ala Pro
225                 230                 235                 240

Ser Asn Asn Asn Ile Gln Phe Val Gly Gly Asp Leu Phe Glu Phe Ile
                245                 250                 255

Pro Ala Ala Asp Val Val Leu Leu Lys Cys Ile Leu His Cys Trp Gln
            260                 265                 270

His Asp Asp Cys Val Lys Ile Met Arg Arg Cys Lys Glu Ala Ile Ser
```

```
            275                 280                 285
Ala Arg Asp Ala Gly Gly Lys Val Ile Leu Ile Glu Val Val Gly
    290                 295                 300

Ile Gly Ser Asn Glu Thr Val Pro Lys Glu Met Gln Leu Leu Phe Asp
305                 310                 315                 320

Val Phe Met Met Tyr Thr Asp Gly Ile Glu Arg Glu His Glu Trp
                325                 330                 335

Lys Lys Ile Phe Leu Glu Ala Gly Phe Ser Asp Tyr Lys Ile Ile Pro
                340                 345                 350

Val Leu Gly Val Arg Ser Ile Ile Glu Val Tyr Pro
            355                 360

<210> SEQ ID NO 8
<211> LENGTH: 432
<212> TYPE: PRT
<213> ORGANISM: Rattus norvegicus

<400> SEQUENCE: 8

Met Ala Pro Gly Arg Glu Gly Glu Leu Asp Arg Asp Phe Arg Val Leu
1               5                   10                  15

Met Ser Leu Ala His Gly Phe Met Val Ser Gln Val Leu Phe Ala Ala
            20                  25                  30

Leu Asp Leu Gly Ile Phe Asp Leu Ala Ala Gln Gly Pro Val Ala Ala
        35                  40                  45

Glu Ala Val Ala Gln Thr Gly Gly Trp Ser Pro Arg Gly Thr Gln Leu
    50                  55                  60

Leu Met Asp Ala Cys Thr Arg Leu Gly Leu Leu Arg Gly Ala Gly Asp
65                  70                  75                  80

Gly Ser Tyr Thr Asn Ser Ala Leu Ser Ser Thr Phe Leu Val Ser Gly
                85                  90                  95

Ser Pro Gln Ser Gln Arg Cys Met Leu Leu Tyr Leu Ala Gly Thr Thr
            100                 105                 110

Tyr Gly Cys Trp Ala His Leu Ala Ala Gly Val Arg Glu Gly Arg Asn
        115                 120                 125

Gln Tyr Ser Arg Ala Val Gly Ile Ser Ala Glu Asp Pro Phe Ser Ala
    130                 135                 140

Ile Tyr Arg Ser Glu Pro Glu Arg Leu Leu Phe Met Arg Gly Leu Gln
145                 150                 155                 160

Glu Thr Trp Ser Leu Cys Gly Gly Arg Val Leu Thr Ala Phe Asp Leu
                165                 170                 175

Ser Arg Phe Arg Val Ile Cys Asp Leu Gly Gly Ser Gly Ala Leu
            180                 185                 190

Ala Gln Glu Ala Ala Arg Leu Tyr Pro Gly Ser Ser Val Cys Val Phe
    195                 200                 205

Asp Leu Pro Asp Val Ile Ala Ala Arg Thr His Phe Leu Ser Pro
210                 215                 220

Gly Ala Arg Pro Ser Val Arg Phe Val Ala Gly Asp Phe Phe Arg Ser
225                 230                 235                 240

Arg Leu Pro Arg Ala Asp Leu Phe Ile Leu Ala Arg Val Leu His Asp
                245                 250                 255

Trp Ala Asp Gly Ala Cys Val Glu Leu Leu Gly Arg Leu His Arg Ala
            260                 265                 270

Cys Arg Pro Gly Gly Ala Leu Leu Leu Val Glu Ala Val Leu Ala Lys
        275                 280                 285
```

```
Gly Gly Ala Gly Pro Leu Arg Ser Leu Leu Leu Ser Leu Asn Met Met
            290                 295                 300

Leu Gln Ala Glu Gly Trp Glu Arg Gln Ala Ser Asp Tyr Arg Asn Leu
305                 310                 315                 320

Ala Thr Arg Ala Gly Phe Pro Arg Leu Gln Leu Arg Arg Pro Gly Gly
                325                 330                 335

Pro Tyr His Ala Met Leu Ala Arg Arg Gly Pro Arg Pro Gly Ile Ile
            340                 345                 350

Thr Gly Val Gly Ser Asn Thr Thr Gly Thr Gly Ser Phe Val Thr Gly
            355                 360                 365

Ile Arg Arg Asp Val Pro Gly Ala Arg Ser Asp Ala Ala Gly Thr Gly
370                 375                 380

Ser Gly Thr Gly Asn Thr Gly Ser Gly Ile Met Leu Gln Gly Glu Thr
385                 390                 395                 400

Leu Glu Ser Glu Val Ser Ala Pro Gln Ala Gly Ser Asp Val Gly Gly
                405                 410                 415

Ala Gly Asn Glu Pro Arg Ser Gly Thr Leu Lys Gln Gly Asp Trp Lys
            420                 425                 430

<210> SEQ ID NO 9
<211> LENGTH: 346
<212> TYPE: PRT
<213> ORGANISM: Gallus gallus

<400> SEQUENCE: 9

Met Asp Ser Thr Glu Asp Leu Asp Tyr Pro Gln Ile Ile Phe Gln Tyr
1               5                   10                  15

Ser Asn Gly Phe Leu Val Ser Lys Val Met Phe Thr Ala Cys Glu Leu
            20                  25                  30

Gly Val Phe Asp Leu Leu Leu Gln Ser Gly Arg Pro Leu Ser Leu Asp
            35                  40                  45

Val Ile Ala Ala Arg Leu Gly Thr Ser Ile Met Gly Met Glu Arg Leu
50                  55                  60

Leu Asp Ala Cys Val Gly Leu Lys Leu Leu Ala Val Glu Leu Arg Arg
65                  70                  75                  80

Glu Gly Ala Phe Tyr Arg Asn Thr Glu Ile Ser Asn Ile Tyr Leu Thr
                85                  90                  95

Lys Ser Ser Pro Lys Ser Gln Tyr His Ile Met Met Tyr Tyr Ser Asn
            100                 105                 110

Thr Val Tyr Leu Cys Trp His Tyr Leu Thr Asp Ala Val Arg Glu Gly
            115                 120                 125

Arg Asn Gln Tyr Glu Arg Ala Phe Gly Ile Ser Ser Lys Asp Leu Phe
130                 135                 140

Gly Ala Arg Tyr Arg Ser Glu Glu Glu Met Leu Lys Phe Leu Ala Gly
145                 150                 155                 160

Gln Asn Ser Ile Trp Ser Ile Cys Gly Arg Asp Val Leu Thr Ala Phe
                165                 170                 175

Asp Leu Ser Pro Phe Thr Gln Ile Tyr Asp Leu Gly Gly Gly Gly Gly
            180                 185                 190

Ala Leu Ala Gln Glu Cys Val Phe Leu Tyr Pro Asn Cys Thr Val Thr
            195                 200                 205

Ile Tyr Asp Leu Pro Lys Val Val Gln Val Ala Lys Glu Arg Leu Val
            210                 215                 220

Pro Pro Glu Glu Arg Arg Ile Ala Phe His Gly Asp Phe Phe Lys
225                 230                 235                 240
```

Asp Ser Ile Pro Glu Ala Asp Leu Tyr Ile Leu Ser Lys Ile Leu His
                245                 250                 255

Asp Trp Asp Asp Lys Lys Cys Arg Gln Leu Leu Ala Glu Val Tyr Lys
            260                 265                 270

Ala Cys Arg Pro Gly Gly Val Leu Leu Val Glu Ser Leu Leu Ser
        275                 280                 285

Glu Asp Arg Ser Gly Pro Val Glu Thr Gln Leu Tyr Ser Leu Asn Met
    290                 295                 300

Leu Val Gln Thr Glu Gly Lys Glu Arg Thr Ala Val Glu Tyr Ser Glu
305                 310                 315                 320

Leu Leu Gly Ala Ala Gly Phe Arg Glu Val Gln Val Arg Arg Thr Gly
                325                 330                 335

Lys Leu Tyr Asp Ala Val Leu Gly Arg Lys
                340                 345

<210> SEQ ID NO 10
<211> LENGTH: 341
<212> TYPE: PRT
<213> ORGANISM: Chromobacterium violaceum

<400> SEQUENCE: 10

Met Gly Tyr Ala Ala Pro Gln Ala Arg Gln Ser Asp Lys Lys Ile Phe
1               5                   10                  15

Asp Ile Tyr Phe Gly Phe Leu His Ser Tyr Ala Leu Leu Phe Ala Asp
                20                  25                  30

Glu Val Gly Leu Phe Asp Leu Leu Arg Cys Glu Ala Leu Thr Leu Asp
            35                  40                  45

Gln Val Ser Met Ala Thr Ser Leu Pro Phe Arg Ser Ser Gln Ala Leu
    50                  55                  60

Leu Ser Leu Cys Ala Ser Leu Gly Leu Leu Glu Lys Arg Gly Glu Arg
65                  70                  75                  80

Phe Ala Leu Ser Ala Leu Ala Glu Gly Phe Leu Val Arg Glu Ala Glu
                85                  90                  95

Thr Ser Phe Cys Gly Val Leu Ala Ser Ala Arg Gly Gln Ala Ala Ala
            100                 105                 110

Phe Ser Tyr Asp Phe Phe Lys Ala Ser Leu Leu Lys Gly Glu Ser Gln
    115                 120                 125

Leu Phe Gly Gly Arg Asp Leu Phe Asp Asn Asn Ala Gln Asp Ser Glu
130                 135                 140

His Cys Glu Ile Phe Thr Arg Ala Met His Ser Lys Ser Lys Gly Pro
145                 150                 155                 160

Ala Gln Ala Trp Val Glu Lys Ile Asp Leu Ser Ala His Ala Cys Leu
                165                 170                 175

Leu Asp Val Gly Gly Gly Ser Gly Val His Ala Ile Ser Ala Leu Ala
            180                 185                 190

Arg Trp Pro Asn Leu Asn Ala Val Val Phe Asp Leu Pro Pro Val Cys
    195                 200                 205

Ala Ile Ala Asp Thr Phe Ile Glu Arg Tyr Gln Met Met Ala Arg Ala
210                 215                 220

Gln Thr His Gly Gly Asp Ile Trp Tyr Thr Asp Tyr Pro Phe Ala Asp
225                 230                 235                 240

Ala His Phe Tyr Ser Asp Ile Phe His Asp Trp Pro Leu Glu Arg Cys
                245                 250                 255

Arg Phe Leu Ala Arg Lys Ser Phe Asp Ala Leu Pro Ser Gly Gly Arg

```
                260                 265                 270
Ile Ile Leu His Glu Met Leu Phe Asn Thr Gln Lys Thr Gly Pro Arg
            275                 280                 285

Asn Val Ala Ala Tyr Asn Ala Asn Met Leu Leu Trp Thr Gln Gly Gln
            290                 295                 300

Gln Leu Ser Glu Pro Glu Ala Ala Asp Leu Leu Gln Ala Ala Gly Phe
305                 310                 315                 320

Val Glu Ile Leu Ala Phe Pro Thr Gly Tyr Gly Asp Trp Ser Leu Val
            325                 330                 335

Thr Gly Val Lys Pro
            340

<210> SEQ ID NO 11
<211> LENGTH: 338
<212> TYPE: PRT
<213> ORGANISM: Desulfotomaculum kuznetsovii DSM 6115

<400> SEQUENCE: 11

Met Tyr Thr Gly Glu Thr Arg Phe Ser Pro Ser Gly Trp Tyr Ile Met
1               5                   10                  15

Asp Ile Cys Arg Gly His Trp Ala Ala Gln Val Leu Phe Thr Ala Val
            20                  25                  30

Asp Leu Gly Leu Phe Asp Ile Leu Ala Arg Gly Ala Gln Thr Pro Ala
        35                  40                  45

Arg Val Ala Ala Ala Leu Gly Thr His Pro Glu Ala Thr Ala Arg Leu
    50                  55                  60

Leu Val Ala Leu Glu Gly Leu Gly Leu Val Lys Arg Glu Gly Glu Phe
65                  70                  75                  80

Tyr Arg Asn Ala Pro Leu Ala Gly Arg His Leu Val Arg Gly Gly Asp
                85                  90                  95

Ala Tyr Leu Gly His Ala Val His His Phe Ala Asn Leu Ala Glu Gly
            100                 105                 110

Trp Ser Arg Leu Gly Glu Ala Val Arg Thr Gly Arg Pro Val Gly Phe
        115                 120                 125

Glu Ala Val Glu Arg Ala Asn Tyr Glu Glu Arg Leu Arg Asp Tyr Ile
    130                 135                 140

Leu Ala Met Gly Asp Gln Ala Arg Leu Lys Ala Asp Arg Leu Ala Ala
145                 150                 155                 160

Ala Leu Asp Leu Ser Gly Cys Glu Arg Ile Leu Asp Leu Gly Gly Gly
                165                 170                 175

Pro Gly Val His Thr Val Ala Leu Leu Lys Lys Glu Pro Arg Ala Arg
            180                 185                 190

Ala Thr Ile Leu Asp Leu Ala Pro Thr Leu Lys Ile Thr Arg Glu Leu
        195                 200                 205

Ile Glu Ala Ala Gly Met Met Glu Arg Val Glu Leu Cys Ala Gly Asp
    210                 215                 220

Phe Thr Arg Asp Glu Leu Gly Glu Gly Val Tyr Asp Leu Val Leu Ala
225                 230                 235                 240

Ser Asn Val Val His Ile Tyr Asp Ala Ala Thr Asn Arg Gln Ile Met
                245                 250                 255

Asp Arg Val Phe Arg Ala Leu Arg Pro Gly Gly Gln Val Val Ile His
            260                 265                 270

Asp Tyr Val Leu Ala Glu Glu Pro Ser Leu Glu Ala Ala Leu Phe Asp
        275                 280                 285
```

```
Leu Asn Met Leu Val Gly Thr Leu Thr Gly Arg Val Tyr Gly Val Gln
        290                 295                 300

Glu Met Gly Ser Trp Leu Glu Asp Ala Gly Phe Val Asp Val Thr Tyr
305                 310                 315                 320

His Pro Leu Thr Pro Gly Ser Gly Leu Leu Lys Gly Arg Lys Trp Asn
                325                 330                 335

Asp Lys
```

<210> SEQ ID NO 12
<211> LENGTH: 266
<212> TYPE: PRT
<213> ORGANISM: Xenopus (Silurana) tropicalis

<400> SEQUENCE: 12

```
Met Lys Asn Asn Glu Ala Phe Phe Ser Asn Thr Asp Val Ser Asn Met
1               5                   10                  15

Tyr Leu Val Lys Ser Ser Pro Arg Ser Phe Tyr Gln Met Met Met Tyr
            20                  25                  30

Tyr Ser Lys Thr Ile Tyr Met Cys Trp His Phe Leu Pro Asp Ala Ile
        35                  40                  45

Arg Glu Gly Lys Arg Gln Tyr Glu Arg Ala Phe Gly Ile Thr Ser Glu
    50                  55                  60

Asp Ile Phe Lys Asp Leu Tyr Arg Ser Glu Glu Thr Val Ser Phe
65                  70                  75                  80

Met His His Met Glu Ser Ile Trp His Ile Cys Gly Lys Asp Val Leu
                85                  90                  95

Ala Ala Phe Asp Leu Ser Ser Phe Lys Glu Ile Cys Asp Ile Gly Gly
            100                 105                 110

Cys Ser Gly Gly Leu Ala Lys His Phe Leu Ser Leu Tyr Pro Ser Ser
        115                 120                 125

Ser Val Thr Ile Met Asp Leu Pro Glu Val Val Gln Met Ala Lys Lys
    130                 135                 140

His Phe Ile Thr Asp Gly Asp Ile Val Phe Leu Glu Asp Phe Phe Asn
145                 150                 155                 160

Asp Pro Leu Pro Glu Ser Asp Leu Tyr Ile Leu Ala Arg Ile Ile His
                165                 170                 175

Asp Trp Thr Glu Asp Lys Cys Leu Arg Leu Leu Asn Lys Ile Tyr Lys
            180                 185                 190

Ser Cys Arg Pro Gly Gly Gly Val Leu Leu Val Glu Ala Leu Leu Asn
        195                 200                 205

Glu Asp Arg Ser Gly Pro Leu Ser Ser Gln Met Phe Ser Leu Asn Met
    210                 215                 220

Leu Leu Gln Thr Glu Gly Lys Glu Arg Ser Ala Ser Glu Tyr His Lys
225                 230                 235                 240

Leu Leu Ala Asp Ser Gly Phe Arg Glu Ile Gln Val Lys Ala Thr Gly
                245                 250                 255

Lys Phe Tyr Asp Ala Val Leu Gly Lys Lys
            260                 265
```

<210> SEQ ID NO 13
<211> LENGTH: 341
<212> TYPE: PRT
<213> ORGANISM: Pseudomonas fluorescens

<400> SEQUENCE: 13

```
Met Asp Ser Thr Val His Thr Glu His His Ser Asp Lys Gln Ile Phe
```

```
  1               5                  10                 15
Asp Ile Tyr Phe Gly Phe Ile Asn Thr Tyr Thr Leu Phe Phe Ala Asp
            20                  25                 30

Glu Val Lys Leu Phe Asp Leu Leu Glu Gly Lys Ala Leu Arg Leu Gly
            35                  40                 45

Glu Ile Gly Ser Ala Leu Glu Leu Ala Pro Arg Ala Ala Gln Ala Leu
            50                  55                 60

Val Ala Met Cys Thr Ser Gln Gly Leu Leu Lys Ser Gly Glu Cys
 65              70                  75                 80

Tyr Gly Leu Thr Ser Leu Ala Gln Ala Phe Leu Thr Arg Lys Ser Glu
            85                  90                 95

Thr Ser Phe Ser Gly Val Leu Gln Ser Ala Arg His Lys Glu Asp Ala
           100                 105                110

Phe Ser Tyr Ala Phe Phe Lys Glu Ser Met Leu Ser Gly Glu Ser Gly
           115                 120                125

Leu Phe Gly Glu Thr Asp Leu Phe Glu Asn Asn Ala Gln Asp Gln Leu
130                135                 140

His Ser Glu Ile Phe Thr Lys Ala Met His Ser Lys Ser Lys Gly Pro
145                150                 155                160

Ala Arg Ala Trp Ser Gly Arg Ile Asp Leu Ser Gly Tyr Thr Cys Leu
               165                 170                175

Leu Asp Val Gly Gly Gly Ser Gly Val His Ser Ile Cys Ala Leu Glu
            180                 185                190

Lys Trp Pro Glu Leu Asn Ala Val Ile Phe Asp Leu Pro Tyr Val Cys
            195                 200                205

Asp Ile Ala Asp Thr Tyr Val Glu Gln Tyr Arg Met Ala Gly Arg Ile
            210                 215                220

Thr Thr His Lys Gly Asp Ile Trp Ala Ser Glu Tyr Pro Ala Ala Asp
225                230                 235                240

Val His Leu Tyr Ser Asp Ile Phe His Asp Trp Pro Leu Asp Lys Cys
               245                 250                255

Leu Phe Leu Ala Lys Lys Ser Phe Asp Ala Leu Pro Ser Gly Gly Arg
            260                 265                270

Ile Ile Leu His Glu Met Phe Asn Lys Asp Lys Thr Gly Pro His
            275                 280                285

Asn Val Ala Ala Tyr Asn Ala Asn Met Leu Leu Trp Thr Gln Gly Gln
            290                 295                300

Gln Leu Ser Glu Thr Glu Ile Arg Glu Leu Leu Thr Ile Ala Gly Phe
305                310                 315                320

Arg Asp Ile Thr Val Ser Arg Thr Gln Tyr Gly Asp Trp Ser Leu Ala
            325                 330                335

Thr Gly Ile Lys Tyr
            340

<210> SEQ ID NO 14
<211> LENGTH: 339
<212> TYPE: PRT
<213> ORGANISM: Candidatus Solibacter usitatus

<400> SEQUENCE: 14

Met Thr Pro Asn Leu Pro Asp Ala Ser Pro Val Leu Asp Leu Ile Glu
1               5                  10                 15

Ala Phe Arg Arg Ser Lys Thr Met Phe Thr Ala Leu Ser Met Gly Val
            20                  25                 30
```

```
Phe Asp Thr Leu His Glu Ala Pro Ser Asn Ala Glu Thr Leu Ala Ala
         35                  40                  45

Lys Leu Gly Ala Asn Ala Gly Ala Leu Ala Arg Leu Leu Asp Gly Cys
 50                  55                  60

Ala Ala Leu Gln Leu Leu Gln Lys Arg Asp Gly Leu Tyr Glu Asn Ala
 65                  70                  75                  80

Pro Leu Ser Glu Thr Tyr Leu Tyr Ser Gly Ser Pro His Ser Met Ser
                 85                  90                  95

Gly Tyr Val Arg Tyr Ser Glu Gln Ala Leu Tyr Pro Met Trp Gly Asn
            100                 105                 110

Leu Ala Asp Ala Val Arg Glu Gly Thr Pro Arg Trp Ser Gln Asn Phe
            115                 120                 125

Gly Ile Asp Gly Pro Ile Phe Ser Ala Phe Phe Arg Thr Pro Glu Ala
130                 135                 140

Met Arg Asp Phe Leu Met Gly Met His Gly Phe Gly Met Leu Thr Ser
145                 150                 155                 160

Pro Lys Val Ala Ala Ala Phe Asp Leu Ser Arg Phe Arg Arg Leu Val
                165                 170                 175

Asp Leu Gly Gly Ala Thr Gly His Leu Thr Ile Ala Ala Cys Glu Leu
            180                 185                 190

Tyr Pro Glu Met Arg Gly Val Val Phe Asp Leu Pro Gln Ala Ala Gly
            195                 200                 205

Met Ala Arg Glu Leu Val Glu Arg Ser Ala Ala Ser Ala Arg Val Glu
            210                 215                 220

Ile Val Ser Gly Asp Phe Phe Ala Asp Glu Leu Pro Glu Ala Asp Leu
225                 230                 235                 240

Tyr Tyr Thr Gly Arg Ile Leu His Asp Trp Ser Glu Glu Lys Ile Asp
                245                 250                 255

Arg Leu Leu Ala Arg Ile Val Gln Arg Leu Pro Ser Gly Gly Ala Leu
            260                 265                 270

Leu Ile Gly Glu Lys Leu Leu Ala Glu Asp Gly Val Gly Pro Val Pro
            275                 280                 285

Ala Asn Met Gln Ser Leu Asn Met Leu Val Val Thr Glu Gly Arg Glu
290                 295                 300

Arg Ser Leu Gly Glu Tyr Arg Gly Leu Leu Met Arg Ala Gly Phe Ala
305                 310                 315                 320

Ser Val Glu Gly Arg His Thr Gly Val Ala Leu Asp Ala Ile Leu Ala
                325                 330                 335

Ile Lys Ala

<210> SEQ ID NO 15
<211> LENGTH: 221
<212> TYPE: PRT
<213> ORGANISM: Fenneropenaeus chinensis

<400> SEQUENCE: 15

Met Ser Ser Leu Lys Ser Tyr Asp Asn Thr Asp Pro Leu Val Gln Tyr
 1               5                  10                  15

Cys Val Asn His Ser Leu Arg Leu Thr Asp Val Gln Lys Arg Leu Asn
                20                  25                  30

Asp Ala Thr Leu Gln His Arg Arg Ala Ala Met Leu Gly Ala Pro Glu
         35                  40                  45

Val Leu Gln Leu Asn Ala Asn Ile Met Gln Ala Ile Gly Ala Lys Lys
 50                  55                  60
```

```
Val Leu Asp Ile Gly Val Phe Thr Gly Ala Ser Ser Leu Ser Ala Ala
 65                  70                  75                  80

Leu Ala Leu Pro Pro Asn Gly Lys Val Tyr Ala Leu Asp Ile Ser Glu
                 85                  90                  95

Glu Phe Thr Asn Ile Gly Lys Pro Tyr Trp Glu Glu Ala Gly Val Ser
                100                 105                 110

Asn Lys Ile Ser Leu His Ile Ala Pro Ala Ala Glu Thr Leu Gln Lys
            115                 120                 125

Phe Ile Asp Ala Gly Glu Ala Gly Thr Phe Asp Tyr Ala Phe Ile Asp
130                 135                 140

Ala Asp Lys Glu Ser Tyr Asp Arg Tyr Glu Leu Cys Leu Ile Leu
145                 150                 155                 160

Leu Arg Pro Gly Gly Val Ile Ala Phe Asp Asn Thr Leu Trp Asp Gly
                165                 170                 175

Ala Val Ile Asp Pro Thr Asp Gln Lys Pro Gly Thr Leu Ala Ile Arg
            180                 185                 190

Lys Met Asn Glu Lys Leu Lys Asp Asp Gln Arg Ile Asn Ile Ser Phe
        195                 200                 205

Leu Arg Ile Gly Asp Gly Leu Ser Leu Cys Phe Lys Lys
210                 215                 220
```

<210> SEQ ID NO 16
<211> LENGTH: 363
<212> TYPE: PRT
<213> ORGANISM: Arabidopsis thaliana

<400> SEQUENCE: 16

```
Met Gly Ser Thr Ala Glu Thr Gln Leu Thr Pro Val Gln Val Thr Asp
1               5                   10                  15

Asp Glu Ala Ala Leu Phe Ala Met Gln Leu Ala Ser Ala Ser Val Leu
                20                  25                  30

Pro Met Ala Leu Lys Ser Ala Leu Glu Leu Asp Leu Leu Glu Ile Met
            35                  40                  45

Ala Lys Asn Gly Ser Pro Met Ser Pro Thr Glu Ile Ala Ser Lys Leu
 50                 55                  60

Pro Thr Lys Asn Pro Glu Ala Pro Val Met Leu Asp Arg Ile Leu Arg
 65                 70                  75                  80

Leu Leu Thr Ser Tyr Ser Val Leu Thr Cys Ser Asn Arg Lys Leu Ser
                85                  90                  95

Gly Asp Gly Val Glu Arg Ile Tyr Gly Leu Gly Pro Val Cys Lys Tyr
                100                 105                 110

Leu Thr Lys Asn Glu Asp Gly Val Ser Ile Ala Ala Leu Cys Leu Met
            115                 120                 125

Asn Gln Asp Lys Val Leu Met Glu Ser Trp Tyr His Leu Lys Asp Ala
130                 135                 140

Ile Leu Asp Gly Gly Ile Pro Phe Asn Lys Ala Tyr Gly Met Ser Ala
145                 150                 155                 160

Phe Glu Tyr His Gly Thr Asp Pro Arg Phe Asn Lys Val Phe Asn Asn
                165                 170                 175

Gly Met Ser Asn His Ser Thr Ile Thr Met Lys Lys Ile Leu Glu Thr
            180                 185                 190

Tyr Lys Gly Phe Glu Gly Leu Thr Ser Leu Val Asp Val Gly Gly Gly
        195                 200                 205

Ile Gly Ala Thr Leu Lys Met Ile Val Ser Lys Tyr Pro Asn Leu Lys
210                 215                 220
```

Gly Ile Asn Phe Asp Leu Pro His Val Ile Glu Asp Ala Pro Ser His
225                 230                 235                 240

Pro Gly Ile Glu His Val Gly Gly Asp Met Phe Val Ser Val Pro Lys
            245                 250                 255

Gly Asp Ala Ile Phe Met Lys Trp Ile Cys His Asp Trp Ser Asp Glu
            260                 265                 270

His Cys Val Lys Phe Leu Lys Asn Cys Tyr Glu Ser Leu Pro Glu Asp
        275                 280                 285

Gly Lys Val Ile Leu Ala Glu Cys Ile Leu Pro Glu Thr Pro Asp Ser
        290                 295                 300

Ser Leu Ser Thr Lys Gln Val Val His Val Asp Cys Ile Met Leu Ala
305                 310                 315                 320

His Asn Pro Gly Gly Lys Glu Arg Thr Glu Lys Glu Phe Glu Ala Leu
            325                 330                 335

Ala Lys Ala Ser Gly Phe Lys Gly Ile Lys Val Val Cys Asp Ala Phe
            340                 345                 350

Gly Val Asn Leu Ile Glu Leu Leu Lys Lys Leu
            355                 360

<210> SEQ ID NO 17
<211> LENGTH: 496
<212> TYPE: PRT
<213> ORGANISM: Homo sapiens

<400> SEQUENCE: 17

Met Gln Pro Ala Met Met Met Phe Ser Ser Lys Tyr Trp Ala Arg Arg
1               5                   10                  15

Gly Phe Ser Leu Asp Ser Ala Val Pro Glu Glu His Gln Leu Leu Gly
            20                  25                  30

Ser Ser Thr Ala Ser Thr Phe Leu Lys Leu Asn Lys Pro Asn Ser Gly
        35                  40                  45

Lys Asn Asp Asp Lys Gly Asn Lys Gly Ser Ser Lys Arg Glu Ala Ala
    50                  55                  60

Thr Glu Ser Gly Lys Thr Ala Val Val Phe Ser Leu Lys Asn Glu Val
65                  70                  75                  80

Gly Gly Leu Val Lys Ala Leu Arg Leu Phe Gln Glu Lys Arg Val Asn
            85                  90                  95

Met Val His Ile Glu Ser Arg Lys Ser Arg Arg Arg Ser Ser Glu Val
            100                 105                 110

Glu Ile Phe Val Asp Cys Glu Cys Gly Lys Thr Glu Phe Asn Glu Leu
        115                 120                 125

Ile Gln Leu Leu Lys Phe Gln Thr Thr Ile Val Thr Leu Asn Pro Pro
    130                 135                 140

Glu Asn Ile Trp Thr Glu Glu Glu Leu Glu Asp Val Pro Trp Phe
145                 150                 155                 160

Pro Arg Lys Ile Ser Glu Leu Asp Lys Cys Ser His Arg Val Leu Met
            165                 170                 175

Tyr Gly Ser Glu Leu Asp Ala Asp His Pro Gly Phe Lys Asp Asn Val
            180                 185                 190

Tyr Arg Gln Arg Arg Lys Tyr Phe Val Asp Val Ala Met Gly Tyr Lys
        195                 200                 205

Tyr Gly Gln Pro Ile Pro Arg Val Glu Tyr Thr Glu Glu Glu Thr Lys
    210                 215                 220

Thr Trp Gly Val Val Phe Arg Glu Leu Ser Lys Leu Tyr Pro Thr His

```
                225                 230                 235                 240
Ala Cys Arg Glu Tyr Leu Lys Asn Phe Pro Leu Leu Thr Lys Tyr Cys
                245                 250                 255

Gly Tyr Arg Glu Asp Asn Val Pro Gln Leu Glu Asp Val Ser Met Phe
                260                 265                 270

Leu Lys Glu Arg Ser Gly Phe Thr Val Arg Pro Val Ala Gly Tyr Leu
                275                 280                 285

Ser Pro Arg Asp Phe Leu Ala Gly Leu Ala Tyr Arg Val Phe His Cys
        290                 295                 300

Thr Gln Tyr Ile Arg His Gly Ser Asp Pro Leu Tyr Thr Pro Glu Pro
305                 310                 315                 320

Asp Thr Cys His Glu Leu Leu Gly His Val Pro Leu Leu Ala Asp Pro
                325                 330                 335

Lys Phe Ala Gln Phe Ser Gln Glu Ile Gly Leu Ala Ser Leu Gly Ala
                340                 345                 350

Ser Asp Glu Asp Val Gln Lys Leu Ala Thr Cys Tyr Phe Phe Thr Ile
                355                 360                 365

Glu Phe Gly Leu Cys Lys Gln Glu Gly Gln Leu Arg Ala Tyr Gly Ala
        370                 375                 380

Gly Leu Leu Ser Ser Ile Gly Glu Leu Lys His Ala Leu Ser Asp Lys
385                 390                 395                 400

Ala Cys Val Lys Ala Phe Asp Pro Lys Thr Thr Cys Leu Gln Glu Cys
                405                 410                 415

Leu Ile Thr Thr Phe Gln Glu Ala Tyr Phe Val Ser Glu Ser Phe Glu
                420                 425                 430

Glu Ala Lys Glu Lys Met Arg Asp Phe Ala Lys Ser Ile Thr Arg Pro
                435                 440                 445

Phe Ser Val Tyr Phe Asn Pro Tyr Thr Gln Ser Ile Glu Ile Leu Lys
                450                 455                 460

Asp Thr Arg Ser Ile Glu Asn Val Val Gln Asp Leu Arg Ser Asp Leu
465                 470                 475                 480

Asn Thr Val Cys Asp Ala Leu Asn Lys Met Asn Gln Tyr Leu Gly Ile
                485                 490                 495

<210> SEQ ID NO 18
<211> LENGTH: 448
<212> TYPE: PRT
<213> ORGANISM: Homo sapiens

<400> SEQUENCE: 18

Met Asp Asp Lys Gly Asn Lys Gly Ser Ser Lys Arg Glu Ala Ala Thr
1               5                   10                  15

Glu Ser Gly Lys Thr Ala Val Phe Ser Leu Lys Asn Glu Val Gly Gly
                20                  25                  30

Gly Leu Val Lys Ala Leu Arg Leu Phe Gln Glu Lys Arg Val Asn Met
                35                  40                  45

Val His Ile Glu Ser Arg Lys Ser Arg Arg Arg Ser Ser Glu Val Glu
            50                  55                  60

Ile Phe Val Asp Cys Glu Cys Gly Lys Thr Glu Phe Asn Glu Leu Ile
65              70                  75                  80

Gln Leu Leu Lys Phe Gln Thr Thr Ile Val Thr Leu Asn Pro Pro Glu
                85                  90                  95

Asn Ile Trp Thr Glu Glu Glu Leu Glu Asp Val Pro Trp Phe Pro
                100                 105                 110
```

-continued

Arg Lys Ile Ser Glu Leu Asp Lys Cys Ser His Arg Val Leu Met Tyr
            115                 120                 125

Gly Ser Glu Leu Asp Ala Asp His Pro Gly Phe Lys Asp Asn Val Tyr
130                 135                 140

Arg Gln Arg Arg Lys Tyr Phe Val Asp Val Ala Met Gly Tyr Lys Tyr
145                 150                 155                 160

Gly Gln Pro Ile Pro Arg Val Glu Tyr Thr Glu Glu Thr Lys Thr
                165                 170                 175

Trp Gly Val Val Phe Arg Glu Leu Ser Lys Leu Tyr Pro Thr His Ala
            180                 185                 190

Cys Arg Glu Tyr Leu Lys Asn Phe Pro Leu Leu Thr Lys Tyr Cys Gly
            195                 200                 205

Tyr Arg Glu Asp Asn Val Pro Gln Leu Glu Asp Val Ser Met Phe Leu
210                 215                 220

Lys Glu Arg Ser Gly Phe Thr Val Arg Pro Val Ala Gly Tyr Leu Ser
225                 230                 235                 240

Pro Arg Asp Phe Leu Ala Gly Leu Ala Tyr Arg Val Phe His Cys Thr
                245                 250                 255

Gln Tyr Ile Arg His Gly Ser Asp Pro Leu Tyr Thr Pro Glu Pro Asp
            260                 265                 270

Thr Cys His Glu Leu Leu Gly His Val Pro Leu Leu Ala Asp Pro Lys
            275                 280                 285

Phe Ala Gln Phe Ser Gln Glu Ile Gly Leu Ala Ser Leu Gly Ala Ser
290                 295                 300

Asp Glu Asp Val Gln Lys Leu Ala Thr Cys Tyr Phe Phe Thr Ile Glu
305                 310                 315                 320

Phe Gly Leu Cys Lys Gln Glu Gly Gln Leu Arg Ala Tyr Gly Ala Gly
                325                 330                 335

Leu Leu Ser Ser Ile Gly Glu Leu Lys His Ala Leu Ser Asp Lys Ala
            340                 345                 350

Cys Val Lys Ala Phe Asp Pro Lys Thr Thr Cys Leu Gln Glu Cys Leu
            355                 360                 365

Ile Thr Thr Phe Gln Glu Ala Tyr Phe Val Ser Glu Ser Phe Glu Glu
370                 375                 380

Ala Lys Glu Lys Met Arg Asp Phe Ala Lys Ser Ile Thr Arg Pro Phe
385                 390                 395                 400

Ser Val Tyr Phe Asn Pro Tyr Thr Gln Ser Ile Glu Ile Leu Lys Asp
                405                 410                 415

Thr Arg Ser Ile Glu Asn Val Val Gln Asp Leu Arg Ile Asn Arg Val
            420                 425                 430

His Ser Ser Ala Leu Thr Glu Lys Glu Gly Val Arg Gln Pro Glu Val
            435                 440                 445

<210> SEQ ID NO 19
<211> LENGTH: 428
<212> TYPE: PRT
<213> ORGANISM: Homo sapiens

<400> SEQUENCE: 19

Met Asp Asp Lys Gly Asn Lys Gly Ser Ser Lys Arg Glu Ala Ala Thr
1               5                   10                  15

Glu Ser Gly Lys Thr Ala Val Val Phe Ser Leu Lys Asn Glu Val Gly
                20                  25                  30

Gly Leu Val Lys Ala Leu Arg Leu Phe Gln Glu Lys Arg Val Asn Met
            35                  40                  45

Val His Ile Glu Ser Arg Lys Ser Arg Arg Ser Glu Val Glu
 50                  55                  60

Ile Phe Val Asp Cys Glu Cys Gly Lys Thr Glu Phe Asn Glu Leu Ile
65                  70                  75                  80

Gln Leu Leu Lys Phe Gln Thr Thr Ile Val Thr Leu Asn Pro Pro Glu
                85                  90                  95

Asn Ile Trp Thr Glu Glu Glu Leu Glu Asp Val Pro Trp Phe Pro
            100                 105                 110

Arg Lys Ile Ser Glu Leu Asp Lys Cys Ser His Arg Val Leu Met Tyr
            115                 120                 125

Gly Ser Glu Leu Asp Ala Asp His Pro Gly Phe Lys Asp Asn Val Tyr
    130                 135                 140

Arg Gln Arg Arg Lys Tyr Phe Val Asp Val Ala Met Gly Tyr Lys Tyr
145                 150                 155                 160

Gly Gln Pro Ile Pro Arg Val Glu Tyr Thr Glu Glu Glu Thr Lys Thr
                165                 170                 175

Trp Gly Val Val Phe Arg Glu Leu Ser Lys Leu Tyr Pro Thr His Ala
            180                 185                 190

Cys Arg Glu Tyr Leu Lys Asn Phe Pro Leu Leu Thr Lys Tyr Cys Gly
    195                 200                 205

Tyr Arg Glu Asp Asn Val Pro Gln Leu Glu Asp Val Ser Met Phe Leu
210                 215                 220

Lys Glu Arg Ser Gly Phe Thr Val Arg Pro Val Ala Gly Tyr Leu Ser
225                 230                 235                 240

Pro Arg Asp Phe Leu Ala Gly Leu Ala Tyr Arg Val Phe His Cys Thr
                245                 250                 255

Gln Tyr Ile Arg His Gly Ser Asp Pro Leu Tyr Thr Pro Glu Pro Asp
            260                 265                 270

Thr Cys His Glu Leu Leu Gly His Val Pro Leu Leu Ala Asp Pro Lys
    275                 280                 285

Phe Ala Gln Phe Ser Gln Glu Ile Gly Leu Ala Ser Leu Gly Ala Ser
290                 295                 300

Asp Glu Asp Val Gln Lys Leu Ala Thr Cys Tyr Phe Phe Thr Ile Glu
305                 310                 315                 320

Phe Gly Leu Cys Lys Gln Glu Gly Gln Leu Arg Ala Tyr Gly Ala Gly
                325                 330                 335

Leu Leu Ser Ser Ile Gly Glu Leu Lys His Ala Leu Ser Asp Lys Ala
            340                 345                 350

Cys Val Lys Ala Phe Asp Pro Lys Thr Thr Cys Leu Gln Glu Cys Leu
    355                 360                 365

Ile Thr Thr Phe Gln Glu Ala Tyr Phe Val Ser Glu Ser Phe Glu Glu
370                 375                 380

Ala Lys Glu Lys Met Arg Asp Phe Ala Lys Ser Ile Thr Arg Pro Phe
385                 390                 395                 400

Ser Val Tyr Phe Asn Pro Tyr Thr Gln Ser Ile Glu Ile Leu Lys Asp
                405                 410                 415

Thr Arg Ser Ile Glu Asn Val Val Gln Asp Leu Arg
            420                 425

<210> SEQ ID NO 20
<211> LENGTH: 315
<212> TYPE: PRT
<213> ORGANISM: Homo sapiens

```
<400> SEQUENCE: 20

Met Glu Leu Glu Asp Val Pro Trp Phe Pro Arg Lys Ile Ser Glu Leu
1               5                   10                  15

Asp Lys Cys Ser His Arg Val Leu Met Tyr Gly Ser Glu Leu Asp Ala
            20                  25                  30

Asp His Pro Gly Phe Lys Asp Asn Val Tyr Arg Gln Arg Arg Lys Tyr
        35                  40                  45

Phe Val Asp Val Ala Met Gly Tyr Lys Tyr Gly Gln Pro Ile Pro Arg
    50                  55                  60

Val Glu Tyr Thr Glu Glu Glu Thr Lys Thr Trp Gly Val Val Phe Arg
65                  70                  75                  80

Glu Leu Ser Lys Leu Tyr Pro Thr His Ala Cys Arg Glu Tyr Leu Lys
                85                  90                  95

Asn Phe Pro Leu Leu Thr Lys Tyr Cys Gly Tyr Arg Glu Asp Asn Val
            100                 105                 110

Pro Gln Leu Glu Asp Val Ser Met Phe Leu Lys Glu Arg Ser Gly Phe
        115                 120                 125

Thr Val Arg Pro Val Ala Gly Tyr Leu Ser Pro Arg Asp Phe Leu Ala
130                 135                 140

Gly Leu Ala Tyr Arg Val Phe His Cys Thr Gln Tyr Ile Arg His Gly
145                 150                 155                 160

Ser Asp Pro Leu Tyr Thr Pro Glu Pro Asp Thr Cys His Glu Leu Leu
                165                 170                 175

Gly His Val Pro Leu Leu Ala Asp Pro Lys Phe Ala Gln Phe Ser Gln
            180                 185                 190

Glu Ile Gly Leu Ala Ser Leu Gly Ala Ser Asp Glu Asp Val Gln Lys
        195                 200                 205

Leu Ala Thr Cys Tyr Phe Phe Thr Ile Glu Phe Gly Leu Cys Lys Gln
210                 215                 220

Glu Gly Gln Leu Arg Ala Tyr Gly Ala Gly Leu Leu Ser Ser Ile Gly
225                 230                 235                 240

Glu Leu Lys His Ala Leu Ser Asp Lys Ala Cys Val Lys Ala Phe Asp
                245                 250                 255

Pro Lys Thr Thr Cys Leu Gln Glu Cys Leu Ile Thr Thr Phe Gln Glu
            260                 265                 270

Ala Tyr Phe Val Ser Glu Ser Phe Glu Glu Ala Lys Glu Lys Met Arg
        275                 280                 285

Asp Phe Ala Lys Ser Ile Thr Arg Pro Phe Ser Val Tyr Phe Asn Pro
    290                 295                 300

Tyr Thr Gln Ser Ile Glu Ile Leu Lys Asp Thr
305                 310                 315
```